(12) United States Patent
Farritor et al.

(10) Patent No.: US 7,772,796 B2
(45) Date of Patent: Aug. 10, 2010

(54) ROBOTIC DEVICES WITH AGENT DELIVERY COMPONENTS AND RELATED METHODS

(75) Inventors: Shane M. Farritor, Lincoln, NE (US);
Dmitry Oleynikov, Omaha, NE (US);
Stephen R. Platt, Garland, NE (US);
Mark Rentschler, Omaha, NE (US);
Jason Dumpert, Omaha, NE (US);
Adnan Hadzialic, Sarajevo (BA);
Nathan A. Wood, Papillion, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 285 days.

(21) Appl. No.: 11/947,097

(22) Filed: Nov. 29, 2007

(65) Prior Publication Data
US 2009/0069821 A1    Mar. 12, 2009

Related U.S. Application Data

(63) Continuation-in-part of application No. 11/695,944, filed on Apr. 3, 2007, now Pat. No. 7,492,116, which is a continuation of application No. 11/398,174, filed on Apr. 5, 2006, now Pat. No. 7,199,545, which is a continuation of application No. 10/616,096, filed on Jul. 8, 2003, now Pat. No. 7,042,184, application No. 11/947,097, which is a continuation-in-part of application No. 11/932,516, filed on Oct. 31, 2007, now abandoned, which is a continuation of application No. 11/403,756, filed on Apr. 13, 2006, now Pat. No. 7,339,341, which is a continuation-in-part of application No. 10/616,096, filed on Jul. 8, 2003, now Pat. No. 7,042,184, application No. 11/947,097, which is a continuation-in-part of application No. 11/932,441, filed on Oct. 31, 2007, now abandoned, which is a continuation of application No. 11/552,379, filed on Oct. 24, 2006, now Pat. No. 7,372,229, which is a continuation of application No. 11/338,166, filed on Jan. 24, 2006, now Pat. No. 7,126,303, which is a continuation-in-part of application No. 10/616,096, filed on Jul. 8, 2003, now Pat. No. 7,042,184.

(60) Provisional application No. 60/868,030, filed on Nov. 30, 2006.

(51) Int. Cl.
*B25J 5/00* (2006.01)

(52) U.S. Cl. ............................ 318/568.12; 318/568.11; 600/101; 600/114; 104/138.1; 104/138.2

(58) Field of Classification Search ............ 318/568.12, 318/568.11, 587; 128/899; 104/138.2; 600/102, 600/114
See application file for complete search history.

(56) References Cited

U.S. PATENT DOCUMENTS 3,870,264 A    3/1975  Robinson (Continued)

FOREIGN PATENT DOCUMENTS

JP    07 136173    5/1995

(Continued)

OTHER PUBLICATIONS

U.S. Appl. No. 12/192,663, filed Aug. 15, 2008.

(Continued)

*Primary Examiner*—Paul Ip
(74) *Attorney, Agent, or Firm*—Faegre & Benson LLP

(57) ABSTRACT

Various robotic devices and related medical procedures are disclosed herein. Each of the various robotic devices have an agent delivery component. The devices include mobile robotic devices and fixed base robotic devices as disclosed herein. The agent delivery component can have at least one agent reservoir and a discharge component in fluidic communication with the at least one reservoir.

16 Claims, 18 Drawing Sheets

U.S. PATENT DOCUMENTS

| | | |
|---|---|---|
| 3,989,952 A | 11/1976 | Hohmann |
| 4,278,077 A | 7/1981 | Mizumoto |
| 4,568,311 A | 2/1986 | Miyaki |
| 4,736,645 A | 4/1988 | Zimmer |
| 4,771,652 A | 9/1988 | Zimmer |
| 4,852,391 A | 8/1989 | Ruch et al. |
| 4,896,015 A * | 1/1990 | Taboada et al. ........ 219/121.78 |
| 4,922,755 A | 5/1990 | Oshiro et al. |
| 4,990,050 A | 2/1991 | Tsuge et al. |
| 5,019,968 A | 5/1991 | Wang et al. |
| 5,172,639 A | 12/1992 | Wiesman et al. |
| 5,178,032 A | 1/1993 | Zona et al. |
| 5,187,796 A | 2/1993 | Wang et al. |
| 5,195,388 A | 3/1993 | Zona et al. |
| 5,201,325 A | 4/1993 | McEwen et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,458,583 A | 10/1995 | McNeely et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,623,582 A | 4/1997 | Rosenberg |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,674,030 A | 10/1997 | Sigel |
| 5,728,599 A | 3/1998 | Rostoker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,792,135 A | 8/1998 | Madhani et al. |
| 5,797,900 A | 8/1998 | Madhani et al. |
| 5,807,377 A | 9/1998 | Madhani et al. |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,906,591 A | 5/1999 | Dario et al. |
| 5,907,664 A | 5/1999 | Wang et al. |
| 5,911,036 A | 6/1999 | Wright et al. |
| 5,971,976 A | 10/1999 | Wang et al. |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| D441,862 S | 5/2001 | Cooper et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,309,397 B1 | 10/2001 | Julian et al. |
| 6,309,403 B1 | 10/2001 | Minor et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Okamoto et al. |
| 6,424,885 B1 | 7/2002 | Niemeyer et al. |
| 6,432,112 B2 | 8/2002 | Brock |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,746,443 B1 | 6/2004 | Morley et al. |

| | | |
|---|---|---|
| 6,764,441 B2 * | 7/2004 | Chiel et al. ............ 600/115 |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 * | 8/2004 | Tanrisever ............ 606/45 |
| 6,783,524 B2 | 8/2004 | Anderson et al. |
| 6,785,593 B2 | 8/2004 | Wang et al. |
| 6,788,018 B1 | 9/2004 | Blumenkranz |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sproul |
| 6,832,996 B2 * | 12/2004 | Woloszko et al. ........... 606/41 |
| 6,836,703 B2 | 12/2004 | Wang et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 * | 9/2005 | Davison et al. .......... 606/41 |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 7,025,064 B2 | 4/2006 | Wang et al. |
| 7,027,892 B2 | 4/2006 | Wang et al. |
| 7,039,453 B2 | 5/2006 | Mullick |
| 7,042,184 B2 * | 5/2006 | Oleynikov et al. ...... 318/568.12 |
| 7,048,745 B2 | 5/2006 | Tierney et al. |
| 7,053,752 B2 | 5/2006 | Wang et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez |
| 7,125,403 B2 | 10/2006 | Julian et al. |
| 7,126,303 B2 * | 10/2006 | Farritor et al. ......... 318/568.12 |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 * | 4/2007 | Oleynikov et al. ...... 318/568.12 |
| 7,206,626 B2 | 4/2007 | Quaid |
| 7,206,627 B2 | 4/2007 | Abovitz |
| 7,210,364 B2 | 5/2007 | Ghorbel |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 * | 3/2008 | Oleynikov et al. ...... 318/568.12 |
| 7,372,229 B2 | 5/2008 | Farritor et al. |
| 7,492,116 B2 | 2/2009 | Oleynikov et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0026186 A1 * | 2/2002 | Woloszko et al. ........... 606/41 |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0140392 A1 | 10/2002 | Borenstein et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 * | 4/2003 | Chiel et al. ............ 600/115 |
| 2003/0089267 A1 | 5/2003 | Ghorbel et al. |
| 2003/0092964 A1 | 5/2003 | Kim et al. |
| 2003/0097129 A1 * | 5/2003 | Davison et al. ............ 606/41 |
| 2003/0114731 A1 | 6/2003 | Cadeddu et al. |
| 2003/0144656 A1 * | 7/2003 | Ocel et al. ............ 606/41 |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0106916 A1 | 6/2004 | Quaid et al. |
| 2004/0111113 A1 | 6/2004 | Nakamura et al. |
| 2004/0138552 A1 | 7/2004 | Harel et al. |
| 2004/0140786 A1 | 7/2004 | Borenstein |
| 2004/0153057 A1 * | 8/2004 | Davison ............. 606/41 |
| 2004/0173116 A1 | 9/2004 | Ghorbel et al. |
| 2004/0176664 A1 | 9/2004 | Iddan |
| 2004/0254680 A1 | 12/2004 | Sunaoshi |
| 2004/0267326 A1 * | 12/2004 | Ocel et al. ............. 607/9 |
| 2005/0029978 A1 | 2/2005 | Oleynikov et al. |
| 2005/0064378 A1 | 3/2005 | Toly |
| 2005/0083460 A1 | 4/2005 | Hattori et al. |
| 2005/0096502 A1 | 5/2005 | Khalili |

| | | | |
|---|---|---|---|
| 2005/0165449 A1 | 7/2005 | Cadeddu et al. | |
| 2005/0288555 A1 | 12/2005 | Binmoeller | |
| 2005/0288665 A1* | 12/2005 | Woloszko | 606/41 |
| 2006/0046226 A1 | 3/2006 | Bergler et al. | |
| 2006/0119304 A1 | 6/2006 | Farritor et al. | |
| 2006/0149135 A1 | 7/2006 | Paz | |
| 2006/0152591 A1 | 7/2006 | Lin | |
| 2006/0195015 A1 | 8/2006 | Mullick et al. | |
| 2006/0196301 A1 | 9/2006 | Oleynikov et al. | |
| 2006/0198619 A1 | 9/2006 | Oleynikov et al. | |
| 2006/0258954 A1 | 11/2006 | Timberlake et al. | |
| 2007/0032701 A1 | 2/2007 | Fowler et al. | |
| 2007/0043397 A1* | 2/2007 | Ocel et al. | 607/10 |
| 2007/0080658 A1 | 4/2007 | Farritor et al. | |
| 2007/0106113 A1* | 5/2007 | Ravo | 600/113 |
| 2007/0123748 A1 | 5/2007 | Meglan | |
| 2007/0156211 A1 | 7/2007 | Ferren et al. | |
| 2007/0225633 A1 | 9/2007 | Ferren et al. | |
| 2007/0225634 A1 | 9/2007 | Ferren et al. | |
| 2007/0241714 A1 | 10/2007 | Okeynikov et al. | |
| 2007/0244520 A1 | 10/2007 | Ferren et al. | |
| 2007/0255273 A1 | 11/2007 | Fernandez et al. | |
| 2008/0004634 A1 | 1/2008 | Farritor et al. | |
| 2008/0015565 A1* | 1/2008 | Davison | 606/37 |
| 2008/0033569 A1 | 2/2008 | Ferren et al. | |
| 2008/0058835 A1 | 3/2008 | Farritor et al. | |
| 2008/0058989 A1 | 3/2008 | Oleynikov et al. | |
| 2008/0103440 A1 | 5/2008 | Ferren et al. | |
| 2008/0111513 A1 | 5/2008 | Farritor et al. | |
| 2008/0132890 A1* | 6/2008 | Woloszko et al. | 606/41 |
| 2008/0164079 A1 | 7/2008 | Jacobsen | |
| 2008/0221591 A1 | 9/2008 | Farritor et al. | |
| 2009/0020724 A1 | 1/2009 | Paffrath | |
| 2009/0048612 A1 | 2/2009 | Farritor et al. | |
| 2009/0054909 A1 | 2/2009 | Farritor et al. | |
| 2009/0069821 A1 | 3/2009 | Farritor et al. | |

FOREIGN PATENT DOCUMENTS

| | | |
|---|---|---|
| JP | 07306155 | 11/1995 |
| WO | WO 02/082979 | 10/2002 |
| WO | 02100256 | 12/2002 |
| WO | WO 2007/149559 | 12/2007 |

OTHER PUBLICATIONS

U.S. Appl. No. 12/324,364, filed Nov. 26, 2008.
International Search Report and Written Opinion from international application No. PCT/US2007/089191, mailed Nov. 10, 2008, 20 pp.
International Search Report and Written Opinion of international application No. PCT/US2008/073369, mailed Nov. 12, 2008, 12 pp.
International Search Report and Written Opinion of international application No. PCT/US2008/073334, mailed Jan. 12, 2009, 11 pp.
Office Action dated Aug. 21, 2006, received in related case U.S. Appl. No. 11/403,756, 6 pp.
Applicant Response to Office Action dated Aug. 21, 2006, in related case U.S. Appl. No. 11/403,756, filed Nov. 21, 2006, 52 pp.
Preliminary Amendment filed Apr. 11, 2007, in related case U.S. Appl. No. 11/403,756, 7 pp.
RCE and Amendment filed Jun. 13, 2007, in related case U.S. Appl. No. 11/403,756, 8 pp.
Office Action dated Aug. 18, 2006, received in related case U.S. Appl. No. 11/398,174, 6 pp.
Applicant Response to Office Action dated Aug. 18, 2006, in related case U.S. Appl. No. 11/398,174, filed Nov. 7, 2006, 8 pp.
Examiner Interview Summary dated Nov. 30, 2006, in related case U.S. Appl. No. 11/398,174, 2 pp.
Office Action dated Oct. 29, 2007, received in related case U.S. Appl. No. 11/695,944, 6 pp.
Applicant Response to Office Action dated Oct. 29, 2007, in related case U.S. Appl. No. 11/695,944, filed Jan. 22, 2008, 6 pp.
Examiner Interview Summary dated May 9, 2008, in related case U.S. Appl. No. 11/695,944, 1 pg.
Examiner Interview Summary dated Aug. 6 and Aug. 12, 2008, in related case U.S. Appl. No. 11/695,944, 1 pg.
Applicant Amendment after Notice of Allowance under Rule 312, filed Aug. 25, 2008, in related case U.S. Appl. No. 11/695,944, 6 pp.
Response to Rule 312 Amendment in related case U.S. Appl. No. 11/695,944, dated Jan. 12, 2009, 2 pp.
Office Action dated Oct. 9, 2008, received in related case U.S. Appl. No. 11/932,441, 4 pp.
Office Action dated Apr. 17, 2007, received in related case U.S. Appl. No. 11/552,379, 5 pp.
Applicant Response to Office Action dated Apr. 17, 2007, in related case U.S. Appl. No. 11/552,379, filed Aug. 8, 2007, 7 pp.
Preliminary Amendment filed Jul. 30, 2008, in related case U.S. Appl. No. 12/171,413, 4 pp.
International Preliminary Report on Patentability from related case PCT/US2007/014567, mailed Jan. 8, 2009, 11 pp.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Abbou et al., "Laparoscopic Radical Prostatectomy with a Remote Controlled Robot," *The Journal of Urology*, Jun. 2001, 165: 1964-1966.
Fraulob et al., "Miniature assistance module for robot-assisted heart surgery," *Biomed. Tech.* 2002, 47 Suppl. 1, Pt. 1, 4 pp.
Guber et al., "Miniaturized Instrument Systems for Minimally Invasive Diagnosis and Therapy," *Biomedizinische Technik*, 2002, Band 47, Erganmngsband 1: 198-201.
Thomann et al., "The Design of a new type of Micro Robot for the Intestinal Inspection," *Proceedings of the 2002 IEEE/RSJIntl. Conference on Intelligent Robots and Systems EPFL*, Oct. 2002, 1385-1390.
Guo et al., "Fish-like Underwater Microrobot with 3 DOF," *Proceedings of the 2002 IEEE International Conference on Robotics &Automation*, May 2002, 738-743.
Fukuda et al., "Mechanism and Swimming Experiment of Micro Mobile Robot in Water," *Proceedings of the 1994 IEEE International Conference on Robotics and Automation*, 1994, 814-819.
Guo et al., "Micro Active Guide Wire Catheter System- Characteristic Evaluation, Electrical Model and Operability Evalu- ation of Micro Active Catheter," *Proceedings of the 1996 IEEE International Conference on Robotics and Automation*, Apr. 1996, 2226-2231.

Yu et al., "Microrobotic Cell Injection," *Proceedings of the 2001 IEEE International Conference on Robotics & Automation*, May 2001, 620-625.

Ruurda et al., "Robot-assisted surgical systems: a new era in laparoscopic surgery," Ann. *R. Coll. Surg. Engl*, 2002, 84: 223-226.

Menciassi et al., "Robotic Solutions and Mechanisms for a Semi-Autonomous Endoscope," *Proceedings of the 2002 IEEE Intl. Conference on Intelligent Robots and Systems EPFL*, Oct. 2002, 1379-1384.

Ishiyama et al., "Spiral-type Micro-machine for Medical Applications," *2000 International Symposium on Micromechatronic and Human Science*, 2000, 65-69s.

Fearing et al., "Wing Transmission for a Micromechanical Flying Insect," *Proceedings of the 2000 IEEE International Conference on Robotics & Automation*, Apr. 2000, 1509-1516.

Mei et al., "Wireless Drive and Control of a Swimming Microrobot," *Proceedings of the 2002 IEEE International Conference on Robotics & Automation.* May 2002, 1131-1136.

Yu, "M2A™ Capsule Endoscopy A Break-through Diagnostic Tool for Small Intestine Imaging," *Gastroenterology Nursing*, 2001, 25(1): 24-27.

Miller et al., "In-Vivo Stereoscopic Imaging System with Five Degrees-of-Freedom for Minimal Access Surgery," Dept. of Computer Science and Dept. of Surgery, Columbia University, New York, NY, p. 7, no date.

Strong et al., "Efficacy of Novel Robotic Camera vs. A Standard Laparoscopic Camera," *Surgical Innovation*, Westminster Publications, Inc., Dec. 2005, 12(4): 315-318.

Worn et al., "Esprit Project No. 33915: Miniaturized Robot for Micro Manipulation (Miniman)," Miniman Consortium, Mar. 22, 2002, 55 pp.

Meron, "The development of the swallowable video capsule (M2A)," *Gastrointestinal Endoscopy*, 2000, 52(6): 817-819.

Phee et al., "Development of Microrobotic Devices For Locomotion in the Human Gastrointestinal Tract," *International conference on Computational Intelligence*, no date.

Breda et al., "Future developments and perspectives in Lacroscopy," *Eur. Urology*, 2001, 40(1): 84-91.

Allendorf et al., "Postoperative Immune Function Varies Inversely with the Degree of Surgical Trauma in a Murine Model," *Surgical Endoscopy*, 1997, 11: 427-430.

Ang, "Active Tremor Compensation in Handheld Instrument for Microsurgery," *Doctoral dissertation, tech report CMU-RI-TR-04-28, Robotics Institute, Carnegie Mellon University*, May 2004, 150 pp.

Atmel 80C5X2 Core, http://www.atmel.com, 2006.

Bailey et al., "Complications of Laparoscopic Surgery," *Quality Medical Publishers, Inc.*, 1995, 25 pp.

Ballantyne, "Robotic Surgery, Telerobotic Surgery, Telepresence, and Telementoring," *Surgical Endoscopy*, 2002, 16: 1389-1402.

Begos et al., "Laparoscopic Cholecystectomy: From Gimmick to Gold Standard," *J Clin Gastroenterol*, 1994, 19(4): 325-330.

Berg et al., "Surgery with Cooperative Robots," *Medicine Meets Virtual Reality*, Feb. 2007, 1 pg.

Breedveld et al., "Locomotion through the Intestine by means of Rolling Stents," *Proceedings of the ASME Design Engineering Technical Conferences*, 2004, pp. 1-7.

Calafiore et al., "Multiple Arterial Conduits Without Cardiopulmonary Bypass: Early Angiographic Results," *Ann Thorac Surg*, 1999, 67: 450-456.

Camarillo et al., "Robotic Technology in Surgery: Past, Present, and Future," *The American Journal of Surgery*, 2004, 188: 2S-15S.

Çavuşoğlu et al., "Robotics for Telesurgery: Second Generation Berkeley/UCSF Laparoscopic Telesurgical Workstation and Looking Towards the Future Applications," *Industrial Robot: An International Journal*, 2003, 30(1): 22-29.

Çavuşoğlu et al., "Telesurgery and Surgical Simulation: Haptic Interfaces to Real and Virtual Surgical Environments," Touch in virtual environments, IMSC Series in Multimedia, 2001, 28 pp.

Choi et al., "Flexure-based Manipulator for Active Handheld Microsurgical Instrument," *Proceedings of the 27th Annual International Conference of the IEEE Engineering in Medicine and Biology Society (EMBS)*, Sep. 2005.

CrystalEyes, http://www.reald.com, 2007 (Stereo3D visualization for CAVEs, theaters and immersive environments), 1 pg.

Cuschieri, "Technology for Minimal Access Surgery," *BMJ*, 1999, 319:1-6.

Stefanini et al., "Modeling and Experiments on a Legged Microrobot Locomoting in a Tubular, Compliant and Slippery Environment," *Int. Journal of Robotics Research*, May-Jun. 2006, 25(5-6): 551-560.

Dumpert et al., "Stereoscopic In Vivo Surgical Robots," *IEEE Sensors Special Issue on In Vivo Sensors for Medicine*, Jan. 2007, 10 pp.

Dumpert et al., "Improving In Vivo Robot Vision Quality," *Proceedings of Medicine Meets Virtual Reality*, Long Beach, CA, Jan. 26-29, 2005.

Faraz et al., "Engineering Approaches to Mechanical and Robotic Design for Minimally Invasive Surgery (MIS)," *Kluwer Academic Publishers* (Boston), 2000, 13 pp.

Flynn et al, "Tomorrow's Surgery; Micro-motors and Microrobots for Minimally Invasive Procedures," *Minimally Invasive Surgery & Allied Technologies*, 1998, 7(4): 343-52.

Franklin et al., "Prospective Comparison of Open vs. Laparoscopic Colon Surgery for Carcinoma: Five-Year Results," Dis Colon Rectum, 1996, 39: S35-S46.

Fukuda et al., "Micro Active Catheter System with Multi Degrees of Freedom," Proceedings of the IEEE International Conference on Robotics and Automation, May 1994, 2290-2295.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committee," *U.S. Food and Drug Administration*, available at http://www.fda.gov, Finalized: Nov. 7, 2003; Updated: Jun. 24, 2005, 11 pp.

Glukhovsky et al., "The development and application of wireless capsule endoscopy," Int. J. Med. Robot. Comput. Assist. Surgery, 2004, 1(1): 114-123.

Slatkin et al., "The Development of a Robotic Endoscope," *Proceedings of the 1995 IEEE International Conference on Robotics and Automation*, 1995, 162-171.

Hanly et al., "Value of the SAGES Learning Center in introducing new technology, " *Surgical Endoscopy*, 2004, 19(4): 477-483.

Hanly et al., "Robotic Abdominal Surgery," *The American Journal of Surgery*, 2004; 188 (Suppl. to Oct. 1994): 19S-26S.

Heikkinen et al., "Comparison of laparoscopic and open Nissen fundoplication 2 Years after operation: A prospective randomized trial," *Surgical Endoscopy*, 2000, 14: 1019-1023.

Horgan et al., "Technical Report: Robots in Laparoscopic Surgery," *Journal of Laparoendoscopic & Advanced Surgical Techniques*, 2001, 11(6): 415-419.

Jagannath et al., "Peroral transgastric endoscopic ligation of fallopian tubes with long-term survival in a porcine model," *Gastrointestinal Endoscopy*, 2005, 61(3): 449-453.

Kalloo et al., "Flexible transgastric peritoneoscopy: a novel approach to diagnostic and therapeutic interventions in the peritoneal cavity," *Gastrointestinal Endoscopy*, 2004, 60(1): 114-117.

Kantsevoy et al., "Transgastric endoscopic splenectomy," *Surgical Endoscopy*, 2006, 20: 522-525.

Kantsevoy et al., "Endoscopic gastrojejunostomy with survival in a porcine model," *Gastrointestinal Endoscopy*, 2005, 62(2): 287-292.

Kim, "Early Experience with Telemanipulative Robot-Assisted Laparoscopic Cholecystectomy Using da Vinci," *Surgical Laparoscopy, Endoscopy & Percutaneous Techniques*, 2002, 12(1): 33-40.

Ko et al., "Per-Oral transgastric abdominal surgery," *Chinese Journal of Digestive Diseases*, 2006, 7: 67-70.

Lafullarde et al., "Laparoscopic Nissen Fundoplication: Five-year Results and Beyond," *Arch/Surg*, Feb. 2001, 136: 180-184.

Liem et al., "Comparison of Conventional Anterior Surgery and Laparoscopic Surgery for Inguinal-hernia Repair," *New England Journal of Medicine*, 1997, 336(22): 1541-1547.

MacFarlane et al., "Force-Feedback Grasper Helps Restore the Sense of Touch in Minimally Invasive Surgery," *Journal of Gastrointestinal Surgery*, 1999, 3: 278-285.

Mack, "Minimally Invasive and Robotic Surgery," *JAMA*, Feb. 2001, 285(5): 568-572.

Mack et al., "Present Role of Thoracoscopy in the Diagnosis and Treatment of Diseases of the Chest," *Ann Thorac Surgery*, 1992, 54: 403-409.

Menciassi et al., "Shape memory alloy clamping devices of a capsule for monitoring tasks in the gastrointestinal tract," J. Micromech. Microeng, 2005, 15: 2045-2055.

Menciassi et al., "Locomotion of a Legged Capsule in the Gastrointestinal Tract: Theoretical Study and Preliminary Technological Results," IEEE Int. Conf. on Engineering in Medicine and Biology, San Francisco, CA, Sep. 2004, 2767-2770.

Micron, http://www.micron.com, 2006, ¼-inch VGA NTSC/PAL CMOS Digital Image Sensor, 98 pp.

Oleynikov et al., "Miniature Robots Can Assist in Laparoscopic Cholecystectomy," *Journal of Surgical Endoscopy*, 2005, 19(4): 473-476.

Oleynikov et al., "In Vivo Camera Robots Provide Improved Vision for Laparoscopic Surgery," *Computer Assisted Radiology and Surgery (CARS)*, Chicago, IL, Jun. 23-26, 2004b.

Hissink, "Olympus Medical develops capsule camera technology," Dec. 2004, accessed Aug. 29, 2007, http://www.letsgodigital.org , 3 pp.

Park et al., "Experimental studies of transgastric gallbladder surgery: cholecystectomy and cholecystogastric anastomosis (videos)," *Gastrointestinal Endoscopy*, 2005, 61(4): 601-606.

Patronik et al., "Preliminary evaluation of a mobile robotic device for navigation and intervention on the beating heart," *Computer Aided Surgery*, Jul. 2005, 10(4): 225-232.

Patronik et al., "Crawling on the Heart: A Mobile Robotic Device for Minimally Invasive Cardiac Interventions," *MICCAI*, 2004, 9-16.

Phee et al., "Analysis and Development of Locomotion Devices for the Gastrointestinal Tract," *IEEE Transaction on Biomedical Engineering*, Jun. 2002, 49(6): 613-616.

Platt et al., "In Vivo Robotic Cameras can Enhance Imaging Capability During Laparoscopic Surgery," in the *Proceedings of the Society of American Gastrointestinal Endoscopic Surgeons (SAGES) Scientific Conference*, Ft. Lauderdale, FL, Apr. 13-16, 2005, 1 pg.

Rentschler et al., "In vivo Robotics during the NEEMO 9 Mission," *Medicine Meets Virtual Reality*, Feb. 2007, 1 pg.

Rentschler et al., "An In Vivo Mobile Robot for Surgical Vision and Task Assistance," *ASME Journal of Medical Devices*, Mar. 2007, 1: 23-29.

Rentschler et al., "Mechanical Design of Robotic In Vivo Wheeled Mobility," *ASME Journal of Mechanical Design*, 2006a, 1-11.

Rentschler et al., "Mobile In Vivo Camera Robots Provide Sole Visual Feedback for Abdominal Exploration and Cholecystectomy," *Journal of Surgical Endoscopy*, 2006b, 20(1): 135-138.

Rentschler et al., "Modeling, Analysis, and Experimental Study of In Vivo Wheeled Robotic Mobility," *IEEE Transactions on Robotics*, 22(2): 308-321, 2006c.

Rentschler et al., "Natural Orifice Surgery with an Endoluminal Mobile Robot," *The Society of American Gastrointestinal Endoscopic Surgeons*, Dallas, TX, Apr. 2006d.

Rentschler et al., "Mobile In Vivo Biopsy and Camera Robot," *Studies in Health and Informatics—Medicine Meets Virtual Reality*, 2006e, 119: 449-454, IOS Press, Long Beach, CA.

Rentschler et al., "Toward In Vivo Mobility," *Studies in Health Technology and Informatics—Medicine Meets Virtual Reality*, ISO Press, Long Beach, CA, 2005a, 111: 397-403.

Rentschler et al., "Mobile In Vivo Robots Can Assist in Abdominal Exploration," in the *Proceedings of the Society of American Gastrointestinal Endoscopic Surgeons (SAGES) Scientific Conference* Ft. Lauderdale, FL, Apr. 13-16, 2005b.

Rentschler et al., "In Vivo Robots for Laparoscopic Surgery," *Studies in Health Technology and Informatics—Medicine Meets Virtual Reality*, ISO Press, Newport Beach, CA, 2004a, 98: 316-322.

Rentschler et al., "Theoretical and Experimental Analysis of In Vivo Wheeled Mobility," *ASME Design Engineering Technical Conferences: 28th Biennial Mechanisms and Robotics Conference*, Salt Lake City, Utah, Sep. 28-Oct. 2, 2004: 1-9.

Riviere et al., "Toward Active Tremor Canceling in Handheld Microsurgical Instruments," IEEE Transactions on Robotics and Automation, Oct. 2003, 19(5): 793-800.

Rosen et al., "Spherical Mechanism Analysis of a Surgical Robot for Minimally Invasive Surgery—Analytical and Experimental Approaches," Studies in Health Technology and Informatics—Medicine Meets Virtual Reality, pp. 442-448, Jan. 2005.

Rosen et al., "The BlueDRAGON—A System of Measuring the Kinematics and the Dynamics of Minimally Invasive Surgical Tools In-Vivo," *Proc. of the 2002 IEEE International Conference on Robotics and Automation*, Washington, DC, May 2002: 1876-1881.

Rosen et al., "Task Decomposition of Laparoscopic Surgery for Objective Evaluation of Surgical Residents' Learning Curve Using Hidden Markov Model," *Computer Aided Surgery*, 2002, 7: 49-61.

Rosen et al., "Objective Laparoscopic Skills Assessments of Surgical Residents Using Hidden Markov Models Based on Haptic Information and Tool/Tissue Interactions," *Studies in Health Technology and Informatics—Medicine Meets Virtual Reality*, Jan. 2001.

Ruurda et al., "Feasibility of Robot-Assisted Laparoscopic Surgery," *Surgical Laparoscopy, Endoscopy & Percutaneous Techniques*, 2002, 12(1): 41-45.

Sackier et al., "Robotically assisted laparoscopic surgery," *Surgical Endoscopy*, 1994, 8: 63-66.

Satava, "Surgical Robotics: The Early Chronicles," *Surgical Laparoscopy, Endoscopy & Percutaneous Techniques*, 2002, 12(1): 6-16.

Schurr et al., "Robotics and Telemanipulation Technologies for Endoscopic Surgery," *Surgical Endoscopy*, 2000, 14: 375-381.

Sharp LL-151-3D, http://www.sharp3d.com, 2006, 2 pp.

Stiff et al., "Long-term Pain: Less Common After Laparoscopic than Open Cholecystectomy," *British Journal of Surgery*, 1994, 81: 1368-1370.

Suzumori et al., "Development of Flexible Microactuator and its Applications to Robotics Mechanisms," *Proceedings of the IEEE International Conference on Robotics and Automation*, 1991.

Taylor et al., "A Telerobotic Assistant for Laparoscopic Surgery," *IEEE Eng Med Biol*, 1995, 279-87.

Tendick et al., "Applications of Micromechatronics in Minimally Invasive Surgery," *IEEE/ASME Transactions on Mechatronics*, 1998, 3(1): 34-42.

Way et al., "Fundamentals of Laparoscopic Surgery," *Churchill Livingstone Inc.*, 1995, 14 pp.

Oleynikov et al., "In Vivo Robotic Laparoscopy," *Surgical Innovation*, Jun. 2005, 12(2): 177-181.

Rentschler et al., "In vivo Mobile Surgical Robotic Task Assistance," University of Nebraska Medical Center, 1 pg.

Rentschler et al., "Mobile In Vivo Biopsy Robot," *IEEE International Conference on Robotics and Automation*, Orlando, Florida, May 2006, 4155-4160.

O'Neill, "Surgeon takes new route to gallbladder," *The Oregonian*, Jun. 2007, 2 pp.

Patronik et al., Development of a Tethered Epicardial Crawler for Minimally Invasive Cardiac Therapies, *IEEE*, 2004, 239-240.

Rosen et al., "Force Controlled and Teleoperated Endoscopic, Grasper for Minimally Invasive Surgery—Experimental Performance Evaluation," *IEEE Transactions of Biomedical Engineering*, Oct. 1999, 46(10): 1212-1221.

Salky, "What is the Penetration of Endoscopic Techniques into Surgical Practice?" *Digestive Surgery*, 2000, 17: 422-426.

Dakin et al., "Comparison of laparoscopic skills performance between standard instruments and two surgical robotic systems," *Surg Endosc*, 2003, 17: 574-579.

Nio et al., "Efficiency of manual vs. robotical (Zeus) assisted laparoscopic surgery in the performance of standardized tasks," *Surg Endosc*, 2002, 16: 412-415.

Melvin et al., "Computer-Enhanced vs. Standard Laparoscopic Antireflux Surgery," *J Gastrointest Surg*, 2002, 6: 11-16.

Park et al., "Trocar-less Instrumentation for Laparoscopy: Magnetic Positioning of Intra-abdominal Camera and Retractor," *Ann Surg*, Mar. 2007, 245(3): 379-384.

Peters, "Minimally Invasive Colectomy: Are the Potential Benefits Realized?" *Dis Colon Rectum 1993*, 36: 751-756.

Gong et al., "Wireless endoscopy," *Gastrointestinal Endoscopy*, 2000, 51(6): 725-729.

Bauer et al., "Case Report: Remote Percutaneous Renal Access Using a New Automated Telesurgical Robotic System," *Telemedicine Journal and e-Health* 2001, 4: 341-347.

Kang et al., "Robotic Assistants Aid Surgeons During Minimally Invasive Procedures," *IEEE Engineering in Medicine and Biology*, Jan./Feb. 2001, 94-104.

Schwartz, "In the Lab: Robots that Slink and Squirm," *The New York Times*, Mar. 27, 2007, 4 pp.

Breedveld et al., "Design of Steerable Endoscopes to Improve the Visual Perception of Depth During Laparoscopic Surgery," *ASME*, Jan. 2004, 126: 1-5.

Fireman et al., "Diagnosing small bowel Crohn's disease with wireless capsule endoscopy," *Gut* 2003, 52: 390-392.

Grady, "Doctors Try New Surgery for Gallbladder Removal," *The New York Times*, Apr. 20, 2007, 3 pp.

Peirs et al., "A miniature manipulator for integration in a self-propelling endoscope," *Sensors and Actuators A*, 2001, 92: 343-349.

Abbott et al., "Design of an Endoluminal NOTES Robotic System," *Proceedings of the 2007 IEEE Conference on intelligent Robots and Systems*, 2007, 410-416.

Falcone et al., "Robotic Surgery," *Clin. Obstet. Gynecol.* 2003, 46(1): 37-43.

Li et al., (2000), "Microvascular Anastomoses Performed in Rats Using a Microsurgical Telemanipulator," *Comp. Aid. Surg.* 5:326-332.

Southern Surgeons Club, (1991), "A prospective analysis of 1518 laparoscopic cholecystectomies," *N. Engl. J. Med.* 324 (16): 1073-1078.

Wolfe et al, (1991), "Endoscopic Cholecystectomy, An Analysis of Complications," *Arch. Surg.* 126:1192-1196.

Schippers et al., (1996), "Requirements and Possibilities of Computer-Assisted Endoscopic Surgery," *Computer Integrated Surgery: Technology and Clinical Applications*, pp. 561-565.

Kazemier et al., (1998), "Vascular Injuries During Laparoscopy," *J. Am. Coll. Surg.* 186(5):604-5.

Leggett et al., (2002), "Aortic injury during laparoscopic fundoplication—An underreported complication," *Surg. Endoscopy* 16(2):362.

Munro, (2002), "Laparoscopic access: complications, technologies, and techniques," *Curr. Opin. Obstet. Gynecol.*, 14(4):365-74.

Orlando et al., (2003), "Needle and Trocar Injuries in Diagnostic Laparoscopy under Local Anesthesia: What Is the True Incidence of These Complications?" *Journal of Laparoendoscopic & Advanced Surgical Techniques* 13(3):181-184.

Tendick et al., (1993), "Sensing and Manipulation Problems in Endoscopic Surgery: Experiment, Analysis, and Observation," *Presence* 2(1):66-81.

Chanthasopeephan et al., (2003), "Measuring Forces in Liver Cutting: New Equipment and Experimental Results," *Annals of Biomedical Engineering* 31:1372-1382.

U.S. Appl. No. 11/932,441, filed Nov. 29, 2007, entitled "Robot for Surgical Applications," 33 pp.

U.S. Appl. No. 11/966,741, filed Dec. 28, 2007, entitled "Methods, Systems, and Devices for Surgical Visualization and Device Manipulation," 52 pp.

U.S. Appl. No. 11/947,097, filed Nov. 29, 2007, entitled "Robotic Devices With Agent Delivery Components and Related Methods," 55 pp.

Franzino, "The Laprotek Surgical System and the Next Generation of Robotics," Surg Clin North Am, 2003 83(6): 1317-1320.

Rentschler et al., "Miniature in vivo Robots for Remote and Harsh Environments," IEEE Transactions on Information Technology in Biomedicine, Jan. 2006; 12(1): 66-75.

Smart Pill "Fantastic Voyage: Smart Pill to Expand Testing," http://www.smartpilldiagnostics.com, Apr. 13, 2005, 1 pg.

Olympus, http://www.letsgodigital.org/en/news/articles/story_2150.html, 2004.

International Search Report and Written Opinion of international application No. PCT/US2007/014567, mailed Apr. 28, 2008, 19 pp.

International Search Report and Written Opinion issued in PCT/US2008/069822, mailed Aug. 5, 2009, 10 pages.

\* cited by examiner

ROBOTIC DEVICES WITH AGENT DELIVERY COMPONENTS AND RELATED METHODS

CROSS-REFERENCE TO RELATED APPLICATION(S)

This application claims priority to U.S. Provisional Patent Application Ser. No. 60/868,030, filed Nov. 30, 2006, which is hereby incorporated herein by reference in its entirety. In addition, this application claims priority as a continuation-in-part of U.S. patent application Ser. No. 11/695,944, filed on Apr. 3, 2007, which is a continuation of U.S. patent application Ser. No. 11/398,174, filed on Apr. 5, 2006, which issued on Apr. 3, 2007 as U.S. Pat. No. 7,199,545, which is a continuation of U.S. patent application Ser. No. 10/616,096, filed on Jul. 8, 2003, which issued on May 9, 2006 as U.S. Pat. No. 7,042,184, all of which are hereby incorporated herein by reference in their entireties. Further, this application claims priority as a continuation-in-part of U.S. patent application Ser. No. 11/932,516, filed on Oct. 31, 2007, which is a continuation of U.S. patent application Ser. No. 11/403,756, filed on Apr. 13, 2006, both of which are hereby incorporated herein by reference in their entireties. The application also claims priority as a continuation-in-part of U.S. patent application Ser. No. 11/932,441, filed on Oct. 31, 2007, which is a continuation of U.S. patent application Ser. No. 11/552,379, filed on Oct. 24, 2006, which is a continuation of U.S. patent application Ser. No. 11/338,166, filed on Jan. 24, 2006, which issued on Oct. 24, 2006 as U.S. Pat. No. 7,126,303, all of which are hereby incorporated herein by reference in their entireties.

FIELD OF THE INVENTION

The field of the various inventions disclosed herein relates to robotic devices used for medical procedures and related methods. More specifically, each implementation of the various robotic devices and methods include an agent delivery component.

BACKGROUND OF THE INVENTION

Laparoscopy is minimally invasive surgery (MIS) performed in the abdominal cavity. It has become the treatment of choice for several routinely performed interventions.

However, known laparoscopy technologies are limited in scope and complexity due in part to (1) mobility restrictions resulting from using rigid tools inserted through access ports, and (2) limited visual feedback. That is, long rigid laparoscopic tools inserted through small incisions in the abdomen wall limit the surgeon's range of motion and therefore the complexity of the surgical procedures being performed. Similarly, using a 2-D image from a typically rigid laparoscope inserted through a small incision limits the overall understanding of the surgical environment. Further, current technology requires a third port to accommodate a laparoscope (camera), and each new viewpoint requires an additional incision.

Robotic systems such as the da Vinci® Surgical System (available from Intuitive Surgical, Inc., located in Sunnyvale, Calif.) have been developed to address some of these limitations using stereoscopic vision and more maneuverable end effectors. However, da Vinci® is still restricted by the access ports. Further disadvantages include the size and high cost of the da Vinci® system, the fact that the system is not available in most hospitals and the system's limited sensory and mobility capabilities. In addition, most studies suggest that current robotic systems such as the da Vinci® system offer little or no improvement over standard laparoscopic instruments in the performance of basic skills. See Dakin, G. F. and Gagner, M. (2003) "Comparison of Laparoscopic Skills Performance Between Standard Instruments and Two Surgical Robotic Systems," *Surgical Endoscopy* 17: 574-579; Nio, D., Bemelman, W. A., den Boer, K. T., Dunker, M. S., Gouma, D. J., and van Gulik, T. M. (2002) "Efficiency of Manual vs. Robotical (Zeus) Assisted Laparoscopic Surgery in the Performance of Standardized Tasks," *Surgical Endoscopy* 16: 412-415; and Melvin, W. S., Needleman, B. J., Krause, K. R., Schneider, C., and Ellison, E. C. (2002) "Computer-Enhanced vs. Standard Laparoscopic Antireflux Surgery," *J. Gastrointest Surg* 6: 11-16. Further, the da Vinci® system and similar systems are implemented from outside the body and will therefore always be constrained to some degree by the limitations of working through small incisions. For example, these small incisions do not allow the surgeon to view or touch the surgical environment directly, and they constrain the motion of the endpoint of the tools and cameras to arcs of a sphere whose center is the insertion point.

There is a need in the art for improved surgical methods, systems, and devices.

BRIEF SUMMARY

One embodiment disclosed herein relates to a robotic device having an agent delivery component.

In one implementation, the device is a mobile robotic device having an agent delivery component. The device can also have a body configured to be disposed within a patient cavity, a translational mobility component, an actuator coupled with the translational mobility component, a power source coupled with the actuator, and a controller component coupled with the actuator. In one embodiment, the mobility component is configured to apply translational pressure on a surface for purposes of mobility or immobility.

Various embodiments of agent delivery components disclosed herein have at least one agent reservoir. Further embodiments have a mixing and discharge component in fluidic communication with the at least one reservoir. The delivery component can also have at least one delivery tube in fluidic communication with the at least one reservoir, a manifold in fluidic communication with the at least one delivery tube, and/or a cannula in fluidic communication with the manifold.

The device, in another embodiment, is a robotic device having a body, an agent delivery component, a rotation component comprising at least one of a pan component and a tilt component; a handle coupled with the body; and a non-attachable support component coupled with the body. According to one embodiment, the body, rotation component, and support component are sized to fit within an animal body cavity.

Various methods of performing a procedure are also disclosed. One implementation includes positioning a robotic device in a cavity inside the patient, operating a controller component to move the robotic device to a desired location within the cavity, and delivering an agent to the desired location with an agent delivery component. In one embodiment, the device has a body, a mobility component, an actuator coupled with the mobility component, a power source, a controller component, and an agent delivery component. In a further embodiment, the method includes using a biopsy tool to obtain a biopsy sample from the desired location prior to delivering the agent.

While multiple embodiments are disclosed, still other embodiments will become apparent to those skilled in the art from the following detailed description, which shows and describes illustrative embodiments of the invention. As will be realized, the embodiments disclosed herein are capable of modifications in various obvious aspects, all without departing from the spirit and scope of the various inventions. Accordingly, the drawings and detailed description are to be regarded as illustrative in nature and not restrictive.

DETAILED DESCRIPTION

The present invention relates to various embodiments of robotic devices for use in surgical methods and systems. Generally, the robotic devices are configured to be inserted into and/or positioned in a patient's body, such as a body cavity, for example.

The robotic devices fall into two general categories: mobile devices and stationary or "fixed base" devices. A "mobile device" includes any robotic device configured to move from one point to another within a patient's body via motive force created by a motor in the device. For example, certain embodiments of mobile devices are capable of traversing abdominal organs in the abdominal cavity. A "fixed base device" is any robotic device that is positioned by a user, such as a surgeon.

Figure 1:
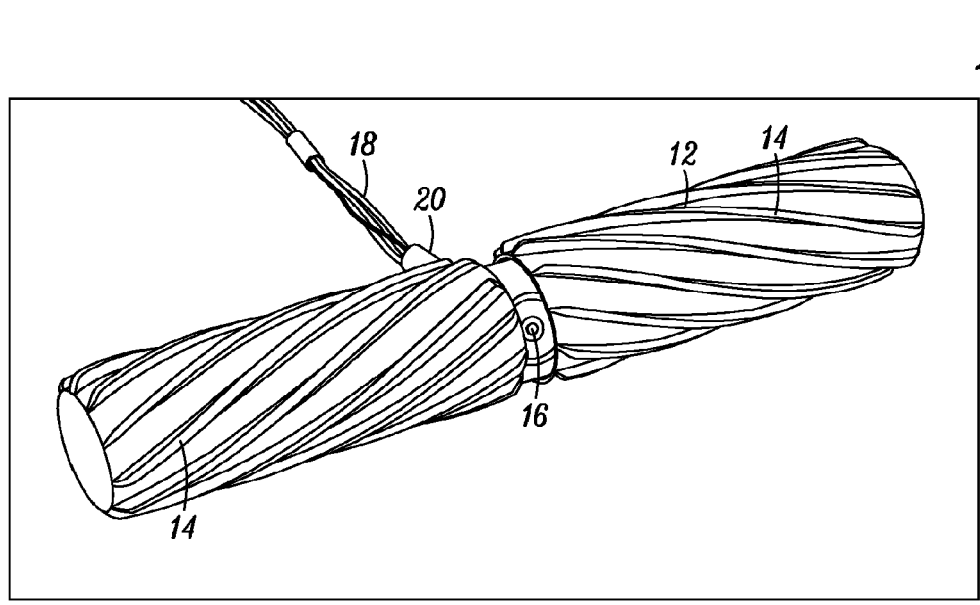
FIG. 1 is a perspective view of a mobile robotic device, according to one embodiment.

FIG. 1 depicts a mobile robotic device 10, according to one embodiment. The device 10 includes a body 12, two wheels 14, a camera 16, and a wired connection component 18 (also referred to herein as a "tether"). Images collected by the camera 16 can be transmitted to a viewing device or other external component via the connection component 18. The device 10 further includes a motor (not shown) configured to provide motive force to rotate the wheels 14, a power supply (not shown) configured to supply power to the motor, and a controller (not shown) operably coupled to the device 10 via the connection component 18. The controller is configured to provide for controlling or operating the device 10 via manipulation of the controller by a user. In one embodiment, the power supply is positioned outside the body and the power is transmitted to the motor via the connection component 18. Alternatively, the power supply is disposed within or on the device 10.

In one alternative embodiment, the device 10 also has a rotation translation component 20 or "tail." The tail 20 can limit counter-rotation and assist the device 10 in translating the rotation of the wheels 14 into movement from one point to another. The "rotation translation component" is any component or element that assists with the translation or conversion of the wheel rotation into movement of the device. In one embodiment, the tail is spring loaded to retract and thus, according to one embodiment, provide for easy insertion of the robotic device 10 through the entry port of a laparoscopic surgical tool.

In another implementation, the device 10 has no tail 20 and the wired connection component 18 or some other component serves to limit counter-rotation.

Alternatively, a mobile robotic device according to another embodiment can also have one or more operational components (also referred to herein as "manipulators") and/or one or more sensor components. In these embodiments, the device may or may not have an imaging component. That is, the device can have any combination of one or more imaging components, one or more operational components, and one or more sensor components.

The operational component might be, for example, biopsy graspers. Further, the one or more sensor components could be chosen from, for example, sensors to measure temperature, blood or other tissue or body fluids, humidity, pressure, and/or pH.

Figure 2:
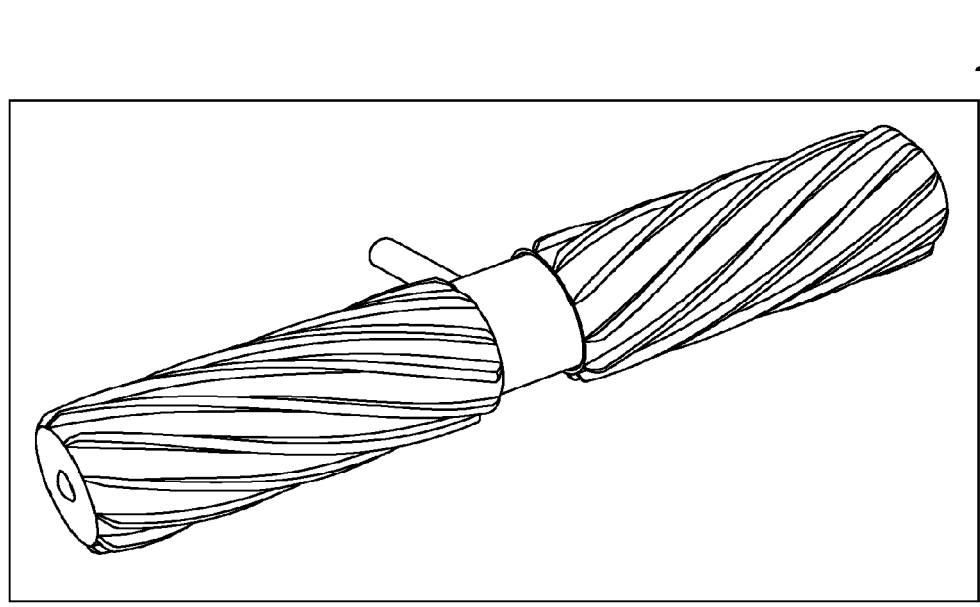
FIG. 2 is a perspective view of a mobile robotic device, according to another embodiment.

In a further alternative, the connection component is a wireless connection component. That is, the controller is wirelessly coupled to, and wirelessly in connection with, the device 10. In such embodiments, the wireless connection component of the device 10 is a transceiver or a transmitter and a receiver to communicate wirelessly with an external component such as a controller. For example, FIG. 2 depicts a wireless mobile robotic device 26, according to one embodiment.

In accordance with one implementation, a mobile robotic device could be used inside the body of a patient to assist with or perform a surgical procedure. In one aspect, the device is sized to fit through standard laparoscopic tools for use during laparoscopic surgery. In another alternative, the device is sized to be inserted through a natural orifice of the patient, such as the esophagus, as will be described in further detail below. In yet another alternative, the device can be sized and configured in any fashion to be used in surgical procedures.

Any of the several embodiments of mobile robotic devices described herein can be used in any number of ways. For example, one implementation of a mobile robotic device could provide visual feedback with a camera system and tissue dissection or biopsy component with a grasper attached to it. Further, such a robot could also be equipped with a sensor suite that could measure pressure, temperature, pH, humidity, etc.

It is understood that a robotic device as described generally above can take on any known configuration and be equipped with any number of sensors, manipulators, imaging devices, or other known components. That is, a robotic device conforming to certain aspects described herein can, in various embodiments, take on many different configurations, such as cylindrical or spherical shapes, or, alternatively, a shape such as that of a small vehicle, and is not limited to the cylindrical robotic devices depicted in FIGS. 1, 2, or 3. Further, there are hundreds of different components known in the art of robotics that can be used in the construction of the robotic devices described herein. For example, there are hundreds controllers, motors, power supplies, wheels, bodies, receivers, transmitters, cameras, manipulators, and sensing devices that can be used in various combinations to construct robotic devices as described herein.

Figure 3A:
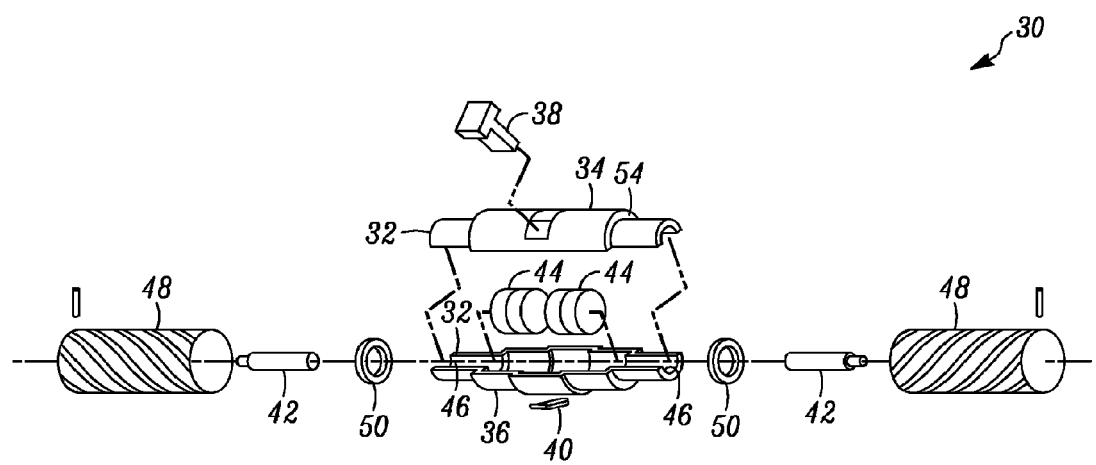
FIG. 3A is an exploded view of a mobile robotic device, according to one embodiment.

FIG. 3A depicts an exploded view of a mobile robotic device 30, according to one embodiment. The device 30 has a body or core component 32 that includes a first portion 34 and a second portion 36. Alternatively, the core component 32 could be a single component. A camera 38 is disposed in the first portion 34, and a tail 40 is attached to the second portion 36. Alternatively, the camera 38 and/or the tail 40 can be attached to either portion 34, 36 or be associated with the device 30 in any other fashion that allows for use of the camera 38 and the tail 40. Further, a motor 42 is disposed in each slot 46 at each end of the body 32 and each motor 42 is operably coupled to one of the wheels 48.

In addition, as shown in FIG. 3A, the device 30 has two wheels 48, each one being rotationally disposed over at least some portion of the body 32. According to one embodiment, two bushings 50 are provided, each disposed between the body 32 and one of the two wheels 48. In one aspect of the invention, the bushing 50 supports the wheel 48 and prevents the wheel 48 from wobbling during rotation. Alternatively, no bushings are provided, or some other type of known support component is provided. In accordance with one implementation, the wheels 48 are coupled to the device 30 via wheel set screws 52.

In one aspect of the invention, the body 32 has a center portion 54 having a radius that is larger than the rest of the body 32. Alternatively, the center portion 54 has the same radius as the rest of the body 32. According to one embodiment, the body 32 can be constructed in any known fashion. For example, according to one embodiment, the body 32 is fabricated via machining or stereolithography.

The device 30 as shown in FIG. 3A also has four batteries 44. According to one embodiment, the batteries 44 are disposed within a cavity of the core component 32. For example, in one embodiment, the batteries 44 are disposed within the center portion 54 of the body 32. Alternatively, the device 30 can have one, two, three, or more than four batteries 44. In one embodiment, each battery 44 is an Energizer™ 309 miniature silver oxide battery. Alternatively, each battery 44 can be any known small battery that can be used within a robotic device. In a further alternative, the power source can be any known power source.

In one implementation, the device 30 also has a wireless connection component (not shown) in the form of transmitter and a receiver (not shown) or a transceiver (not shown) for use in a wireless configuration of the device 30 such that any images collected by the camera 38 can be transmitted to an external component for viewing and/or storage of the image and further such that any control signals can be transmitted from an external controller or other external component to the motor 42 and/or other components of the device 30. Alternatively, the device 30 has a wired connection component (not shown) that is attached to the device 30.

In another implementation, the device 30 can also have a light component (not shown) to illuminate the area to be captured by the imaging component. Alternatively, the device 30 has no light component.

According to one embodiment, a robotic device similar to the device 30 depicted in FIG. 3A can be constructed in the following manner. Any components to be associated with the body 32, such as a camera 38 and a tail 40, are coupled with the body 32. In addition, any components to be disposed within the body 32, such as batteries 44, motors 42, and other electronic components (not shown), are positioned within the body 32. In an embodiment in which the body 32 consists of two portions 34, 36, these components to be associated with or disposed within the body 32 are positioned in or attached to the body 32 prior to the coupling of the two portions 34, 36. According to one embodiment, a bushing 50 is disposed over each end of the body 32. Alternatively, no bushings 50 are provided. Subsequently, the wheels 48 are positioned on the device 30. For example, according to one embodiment, the wheels 48 are positioned on the motor shafts 52.

The device 30 depicted in FIG. 3A, according to one embodiment, is configured to fit through a port in a known laparoscopic surgical tool. For example, in accordance with one implementation, the device 30 is configured to be inserted through a standard 15 mm medical port.

According to another embodiment, the robotic device 30 can be constructed without any sharp edges, thereby reducing damage to the patient during use of the device 30. In a further embodiment, the device 30 is comprised of biocompatible materials and/or materials that are easy to sterilize.

A mobile robotic device conforming to certain characteristics of various embodiments discussed herein has a transport component, which is also referred to herein as a "mobility component." "Transport component" is any component that provides for moving or transporting the device between two points. In one example, the transport component is one or more wheels. For example, the transport components of the mobile robotic devices depicted in FIGS. 1, 2, and 3 are wheels.

Alternatively, a robotic device as described herein can have any known transport component. That is, the transport component is any known component that allows the device to move from one place to another. The present application contemplates use of alternative methods of mobility such as walking components, treads or tracks (such as used in tanks), hybrid components that include combinations of both wheels and legs, inchworm or snake configurations that move by contorting the body of the device, and the like.

According to one embodiment as depicted in FIG. 3A, the robotic device 30 has two wheels 48 independently driven with separate motors 42. According to one embodiment, the motors 42 are direct current motors. In another embodiment, each wheel 48 is attached to the motors 42 through a set of bearings and spur gears. In one implementation, the two separate motors 42 provide forward, reverse and turning capabilities. That is, the two wheels 48 with two separate motors 42 are configured to allow the device 30 to move forward or backward, or to turn. According to one embodiment, the two wheels 48 move the device 30 forward or backward by each wheel 48 rotating at the same speed. In this embodiment, the wheels 48 provide for turning the device 30 by each wheel 48 turning at a different speed or in different directions. That is, the left wheel turns faster than the right wheel when the device 30 turns right, and the right wheel turns faster than the left when the device turns left. In accordance with one implementation, the wheels 48 can also provide for a zero turning radius. That is, one wheel 48 can rotate in one direction while the other wheel 48 rotates in the other direction, thereby allowing the device 30 to turn 180° or 360° while the center portion of device 30 stays in substantially the same location.

Figure 3B:
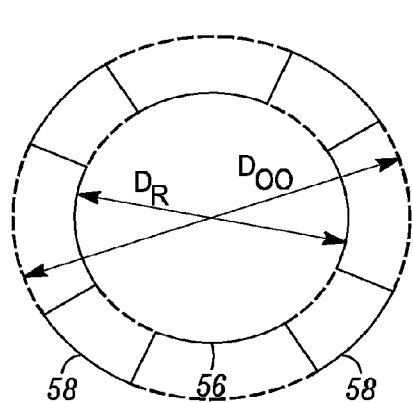
FIG. 3B is a side view of a wheel of a mobile robotic device, according to one embodiment.
Figure 3C:
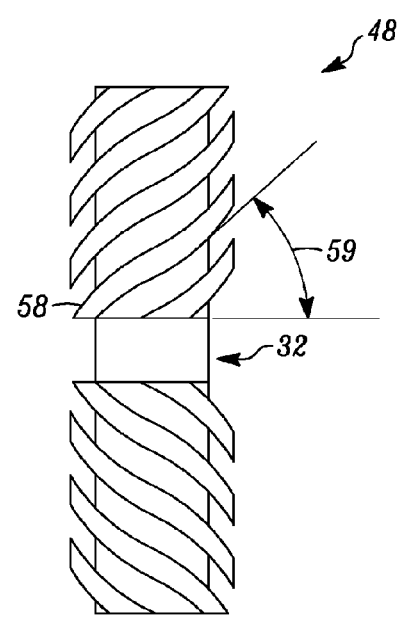
FIG. 3C is a plan view of a wheel of a mobile robotic device, according to one embodiment.

Each wheel 48, according to one implementation, has a surface texture on its exterior surface as shown in FIGS. 3A, 3B, and 3C. According to one embodiment, the surface texture creates traction for the wheel 48 as it moves across a tissue, organ, or other body surface.

FIGS. 3B and 3C depict one embodiment in which the wheels 48 have a surface texture consisting of raised portions 58 (also referred to herein as "grousers") disposed in a particular configuration on the wheels 48. The raised portions 58 are those portions of the wheel 48 that contact the surface that the wheels 48 are traversing.

The raised portion 58, according to one embodiment, defines an outer diameter 58 ($d_{oo}$), while the wheel 48 defines an inner diameter 56 ($d_r$). According to another embodiment, the inner and outer diameters of the wheels in one implementation are 17 mm and 20 mm, respectively. Alternatively, the grouser depth is 1.5 mm, where grouser depth is equal to ($d_{oo}-d_r$)/2. In a further alternative, the diameters and/or the grouser depth are any that would be useful for wheels on the mobile devices disclosed herein.

In another embodiment, the helical profile 59 of the wheels has a pitch of 30° as depicted in FIG. 3C. Alternatively, the helical profile can have a pitch ranging from about 0 degrees to about 90 degrees. In another aspect, the wheels 48 have treads. Alternatively, the surface texture is any surface characteristic that creates traction for the wheel 48.

In accordance with one implementation, the transport component constitutes at least about 80% of the external surface area of the robotic device. Alternatively, the transport component constitutes at least about 90% of the external surface area of the robotic device. In a further alternative, the transport component constitutes from about 80% to about 98% of the external surface area of the robotic device. In yet another alternative, the transport component constitutes any percentage of the external surface area of the robotic device.

The wheels depicted in FIGS. 1, 2, and 3 have a round, tubular-type treaded configuration. Alternatively, virtually any configuration could be employed, such as a round, square, spherical, or triangular configuration.

In addition, the wheels depicted in FIGS. 1, 2, and 3 are comprised of aluminum. Alternatively, the wheels are constructed of rubber or a combination of aluminum and rubber. In a further alternative, virtually any material that allows for traction or mobility can be used to construct the wheel or other transport component. In one embodiment, the material is any material that provides for traction on unusual, slick, hilly, deformable, or irregular surfaces such as any internal tissues, organs such as the liver, stomach, and/or intestines, or other internal surfaces, crevices, and contours of a patient, all of which has different surface properties.

In certain alternative embodiments, the robotic device has one or more sensor components. In various embodiments, such sensor components include, but are not limited to, sensors to measure or monitor temperature, blood, any other bodily fluids, fluid composition, presence of various gases, such as $CO_2$, for example, or other parameters thereof, humidity, electrical potential, heart rate, respiration rate, humidity, pressure, and/or pH. Further, the one or more sensor components can include one or more imaging components, which shall be considered to be a type of sensor component for purposes of this application. The sensors, including imaging devices, can be any such components or devices known in the art that are compatible with the various designs and configurations of the robotic devices disclosed herein.

According to one embodiment, a robotic device having one or more of the sensors described herein assists the user in the performance of a surgical procedure. In accordance with one implementation, the one or more sensors restore some of the natural monitoring or sensing capabilities that are inherently lost when using standard laparoscopic tools. Thus, the one or more sensor components allow the user to perform more complex procedures and/or more accurately monitor the procedure or the patient.

According to one embodiment, the imaging component can be a camera or any other imaging device. The imaging component can help to increase or improve the view of the area of interest (such as, for example, the area where a procedure will be performed) for the user. According to one embodiment, the imaging component provides real-time video to the user.

Current standard laparoscopes use rigid, single view cameras inserted through a small incision. The camera has a limited field of view and its motion is highly constrained. To obtain a new perspective using this prior art technique often requires the removal and reinsertion of the camera through another incision, increasing patient risk. In contrast to such limited imaging, a robotic device having one or more imaging components according to various embodiments described herein eliminates many of the limitations and disadvantages of standard laparoscopy, providing for an expanded and adjustable field of view with almost unlimited motion, thereby improving the user's visual understanding of the procedural area.

As used herein, the terms "imaging component," "camera," and "imaging device" are interchangeable and shall mean the imaging elements and processing circuitry which are used to produce the image signal that travels from the image sensor or collector to a viewing component. According to one embodiment, the image is a moving video image and the viewing component is a standard video viewing component such as a television or video monitor. Alternatively, the image is a still image. In a further alternative, the images are a combination of still and moving video images. The term "image sensor" as used herein means any component that captures images and stores them. In one embodiment, the image sensor is a sensor that stores such images within the structure of each of the pixels in an array of pixels. The terms "signal" or "image signal" as used herein, and unless otherwise more specifically defined, means an image which is found in the form of electrons which have been placed in a specific format or domain. The term "processing circuitry" as used herein refers to the electronic components within the imaging device which receive the image signal from the image sensor and ultimately place the image signal in a usable format. The terms "timing and control circuits" or "circuitry" as used herein refer to the electronic components which control the release of the image signal from the pixel array.

In accordance with one implementation, the imaging component is a small camera. In one exemplary embodiment, the imaging component is a complementary metal oxide semiconductor ("CMOS") digital image sensor such as Model No. MT9V125 from Micron Technology, Inc., located in Boise, Id. Alternatively, the imaging component is a square 7 mm camera. In an alternative example, the camera can be any small camera similar to those currently used in cellular or mobile phones. In another example, the imaging device can be any imaging device currently used in or with endoscopic devices. In one embodiment, the imaging device is any device that provides a sufficient depth of field to observe the entire abdominal cavity.

According to another embodiment, the imaging device can employ any common solid state image sensor including a charged coupled device (CCD), charge injection device (CID), photo diode array (PDA), or any other CMOS, which offers functionality with simplified system interfacing. For example, a suitable CMOS imager including active pixel-type arrays is disclosed in U.S. Pat. No. 5,471,515, which is hereby incorporated herein by reference in its entirety. This CMOS imager can incorporate a number of other different electronic controls that are usually found on multiple circuit boards of much larger size. For example, timing circuits, and special functions such as zoom and anti-jitter controls can be placed on the same circuit board containing the CMOS pixel array without significantly increasing the overall size of the host circuit board. Alternatively, the imaging device is a CCD/CMOS hybrid available from Suni Microsystems, Inc. in Mountain View, Calif.

In accordance with one implementation, the imaging device provides video output in NTSC format. For example, any commercially-available small NTSC video format transmission chips suitable for the devices described herein can be used. Alternatively, any known video output in any known format can be incorporated into any device described herein.

The imaging component, according to one embodiment, has a manual focus adjustment component. Alternatively, the imaging component has a mechanically-actuated adjustable-focus component. A variety of adjustable-focus mechanisms are known in the art and suitable for actuating focusing of many types of known imaging components.

In one embodiment, the imaging component is capable of focusing in range from about 2 mm to infinity. Alternatively, the imaging component can have a focusing range similar to that of any known adjustable focus camera.

Figure 4:
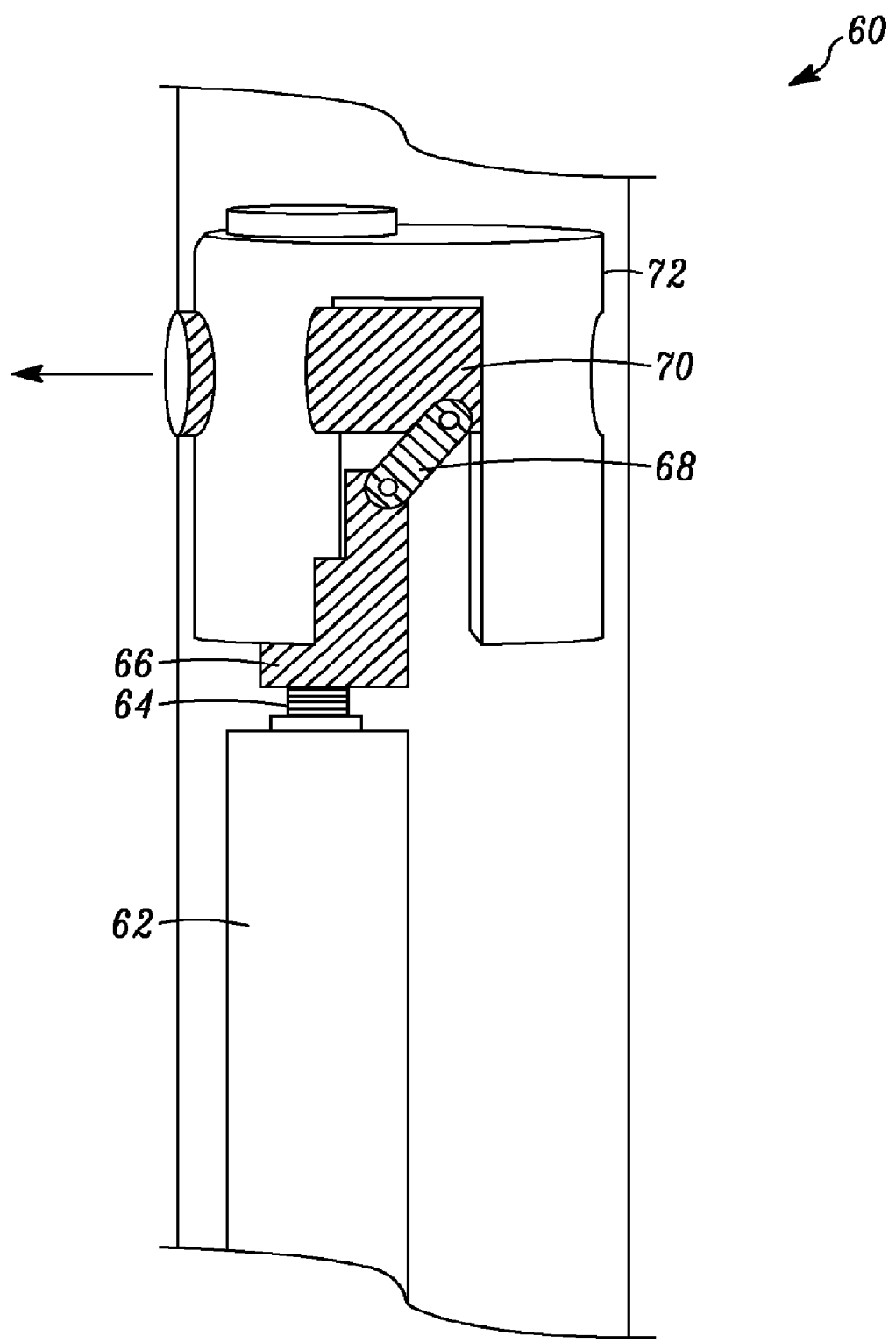
FIG. 4 depicts the adjustable-focus component implemented in a camera robot, according to one embodiment.

Alternatively, the imaging component has an adjustable-focus mechanism 60 as depicted in FIG. 4 that employs a motor 62 that is directly connected to a lead screw 64 which is rotated by motor 62. In this embodiment, as the lead screw 64 rotates, it drives a lead nut 66 up and down. This up-and-down motion is translated by a linkage 68 to a slider 70 that moves left to right. Slider 70 is held in place by a mechanism housing or guide 72. A lens or image sensor mounted to slider 70 can be translated back and forth from left to right to allow adjustable focusing. According to some embodiments, the motor 62 used to power the adjustable-focus mechanism of the imaging component can also be used to power other components of the robotic device, such as, for example, a biopsy component as described in greater detail below.

In accordance with another embodiment, the imaging component can be controlled externally to adjust various characteristics relating to image quality. For example, according to one embodiment, one or more of the following can be adjusted by a user: color, white balance, saturation, and/or any other known adjustable characteristic. According to one embodiment, this adjustment capability can provide quality feedback in poor viewing conditions such as, for example, low lighting.

According to one implementation, any mobile imaging device disclosed herein can have any known lens that can be used with such devices. In one particular embodiment, the lens is model no. DSL756A, a plastic lens available from Sunex, located in Carlsbad, Calif. This embodiment provides only a short depth of field, which requires adjustable-focus capability. To attain this, the lens of this implementation is attached to an actuation mechanism to provide adjustable focus capability. The lens is moved by the actuation mechanism to provide a range of focus from 2 mm to infinity. Alternatively, the lens can be any lens that can be incorporated into any of the imaging devices described herein.

In a further alternative, the imaging component can include an image stabilization component. For example, according to one embodiment, the device could include on-board accelerometer measurements with image motion estimates derived from optical flow to yield base motion estimates, such as are known in the art. Alternatively, the image stabilization component can be any such commercially-available component. Optical flow has been shown to yield reliable estimates of displacements computed across successive image frames. Using these robot base motion estimates, image stabilization algorithm can be used to provide image stabilization. Alternatively, any known image stabilization technology can be incorporated for use with the imaging component.

In certain embodiments, the camera is fixed with respect to the body of the robotic device, such that the position of the robot must be changed in order to change the area to be viewed. Alternatively, the camera position can be changed with respect to the device such that the user can move the camera with respect to the robotic device. According to one embodiment, the user controls the position of the camera using a controller that is operably coupled to the device as described in further detail herein.

The robotic device can also, according to one embodiment, have a lighting component to light the area to be viewed. In one example, the lighting component is an LED light. Alternatively, the lighting component can be any illumination source.

According to one implementation, the camera is disposed on the center portion of the body of the device, as shown in FIG. 3A. Alternatively, the camera can be disposed on any portion of the body. In a further alternative, the camera can be disposed anywhere on the robotic device.

According to one embodiment, the robotic device has one or more operational components. The "operational component," as used herein, is intended to mean any component that performs some action or procedure related to a surgical or exploratory procedure. According to one embodiment, the operational component is also referred to as a "manipulator" and can be a clamp, scalpel, any type of biopsy tool, a grasper, forceps, stapler, cutting device, cauterizing device, ultrasonic burning device, or other similar component, as set forth in further detail herein. In yet another embodiment, the operational component is any device that can perform, or assist in the performance of, any known surgical or exploratory laparoscopic procedure. In one aspect, the one or more operational components assist with procedures requiring high dexterity. In currently known techniques, movement is restricted, as passing the rigid laparoscopic tool through a small incision restricts movement and positioning of the tool tip. In contrast, a robotic device having an operational component inside a cavity is not subject to the same constraints.

In one implementation, the operational component can also include an arm or other positioning component. For example, the operational component can include an arm and a biopsy tool. Alternatively, the operational component can include a positioning component and any operational component as described above.

According to one embodiment, any operational component described or contemplated herein can be an off-the-shelf surgical tool or modified version thereof. Alternatively, any such operational component can be constructed de novo.

Figure 5:
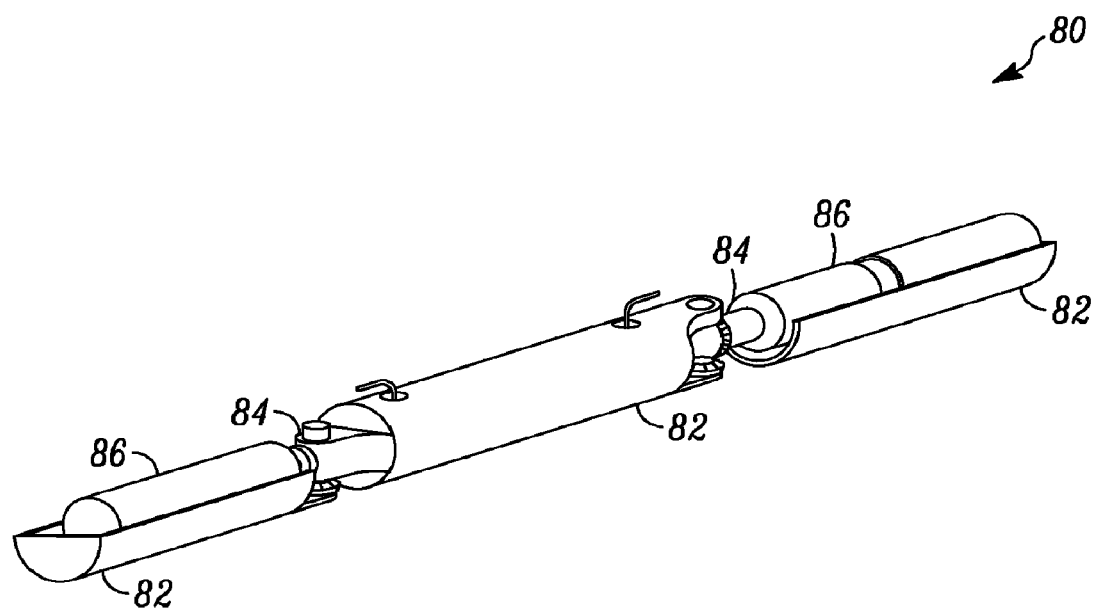
FIG. 5 is a perspective view of a manipulator arm according to one embodiment.
Figure 6:
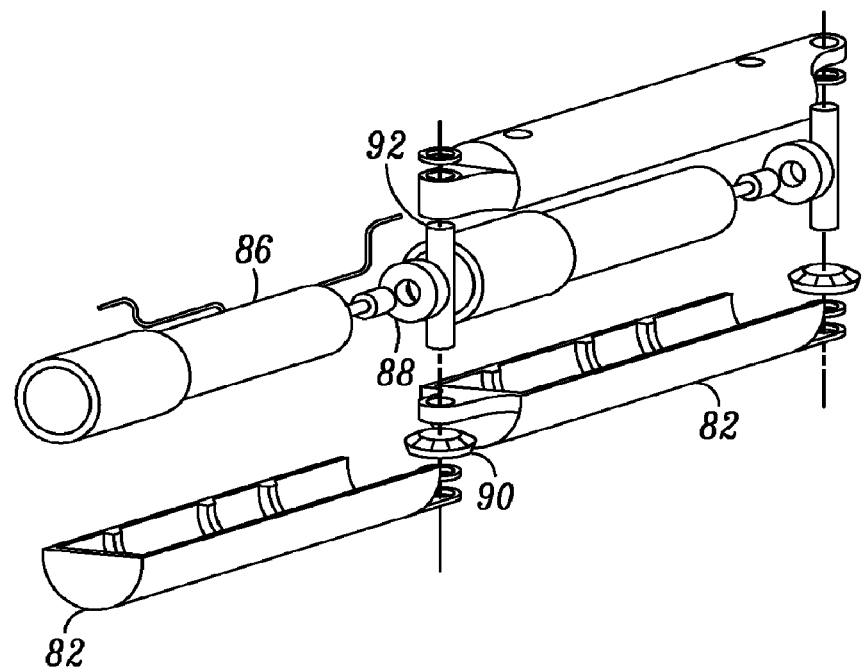
FIG. 6 is an exploded view of a manipulator arm according to one embodiment.

The operational component depicted in FIGS. 5 and 6 is a manipulator arm 80 having three arms or "links" 82, according to one implementation. The arm 80 has two joints 84, each coupled to a motor 86. According to one embodiment, as best depicted in FIG. 6, the links 82 are composed of two halves that attach in only one configuration.

The joints 84 are configured in any known fashion. In one example as depicted in FIGS. 5 and 6, each joint 84 has a gear 88 coupled to the motor, and another gear 90 coupled to a pin 92. In one aspect, the gears are bevel gears. According to one embodiment, the gears are standard miter gears available from Stock Drive Products/Sterling Instruments, located in New Hyde Park, N.Y.

In one implementation, the arm was constructed using stereolithography. According to one embodiment, stereolithography can be used to construct the linkages and the base section out of a cured resin material similar to plastic.

The motor, according to one embodiment, that can be used in the linkages is a DC micromotor with encoders manufactured by MicroMo Electronics, located in Clearwater, Fla. The motor is a 6 V motor having a 15,800 rpm no-load speed, 0.057 oz-in stall torque, and weighed 0.12 oz. The motor has an 8 mm diameter and is 16 mm long. Due to its high no-load speed, a precision planetary gearhead is used. Further description of the motor, gearhead, and an encoder that can be used with the motor are described in U.S. Pat. No. 7,199,545. Alternatively, the arm can use a low voltage motor, such as a 3 V motor.

In one implementation, the arm has an encoder used for the indication and control of both shaft velocity and the direction of rotation, as well as for positioning. In one embodiment, the encoder is a 10 mm magnetic encoder. It is 16.5 mm long, but only adds 11.5 mm to the total length of the assembly.

Figure 7:
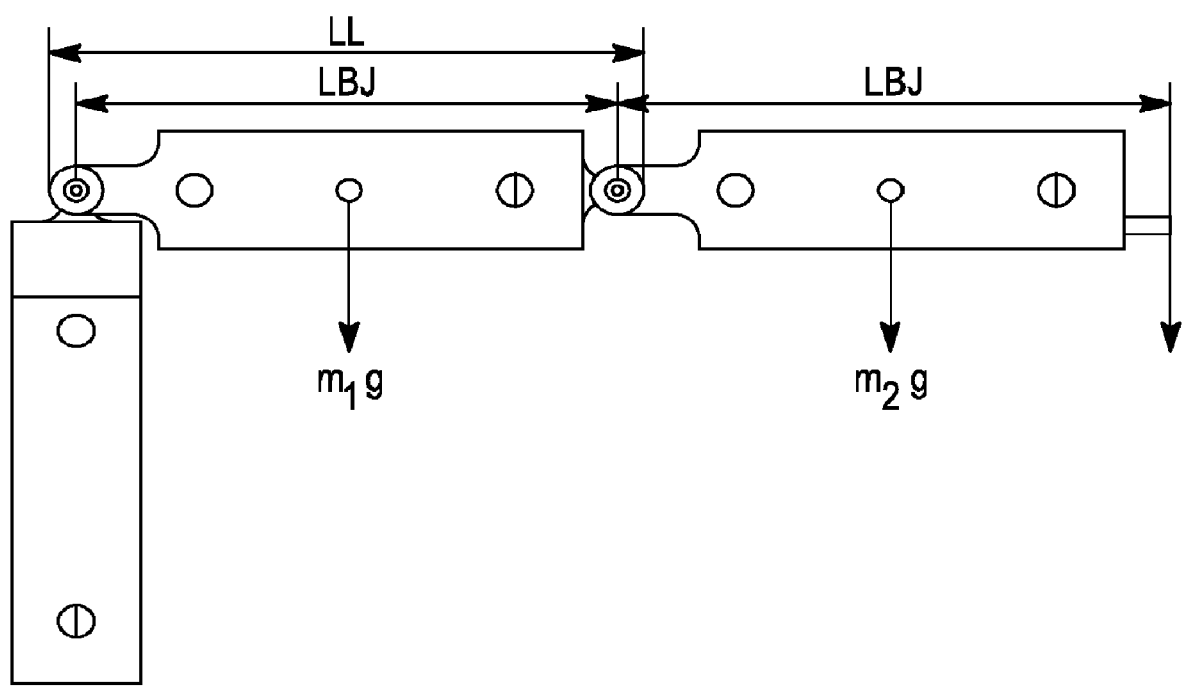
FIG. 7 is a model of one embodiment of a manipulator arm labeled with the parameters used to determine properties of the links.

FIG. 7A shows a schematic of one manipulator embodiment with $L_L$, $L_{BJ}$, $M_1$, $M_2$, $m_1g$, $m_2g$ and $W_p$ labeled. Without being limiting, the schematic was used for calculating various characteristics relating to one manipulator embodiment and is explained in further detail in U.S. Pat. No. 7,199,545. Based on the testing, it was determined that for this particular embodiment, a reduction ratio off 64:1 provides sufficient torque while optimizing the design. Alternatively, precision gears with other reduction ratios may be used.

Figure 8:
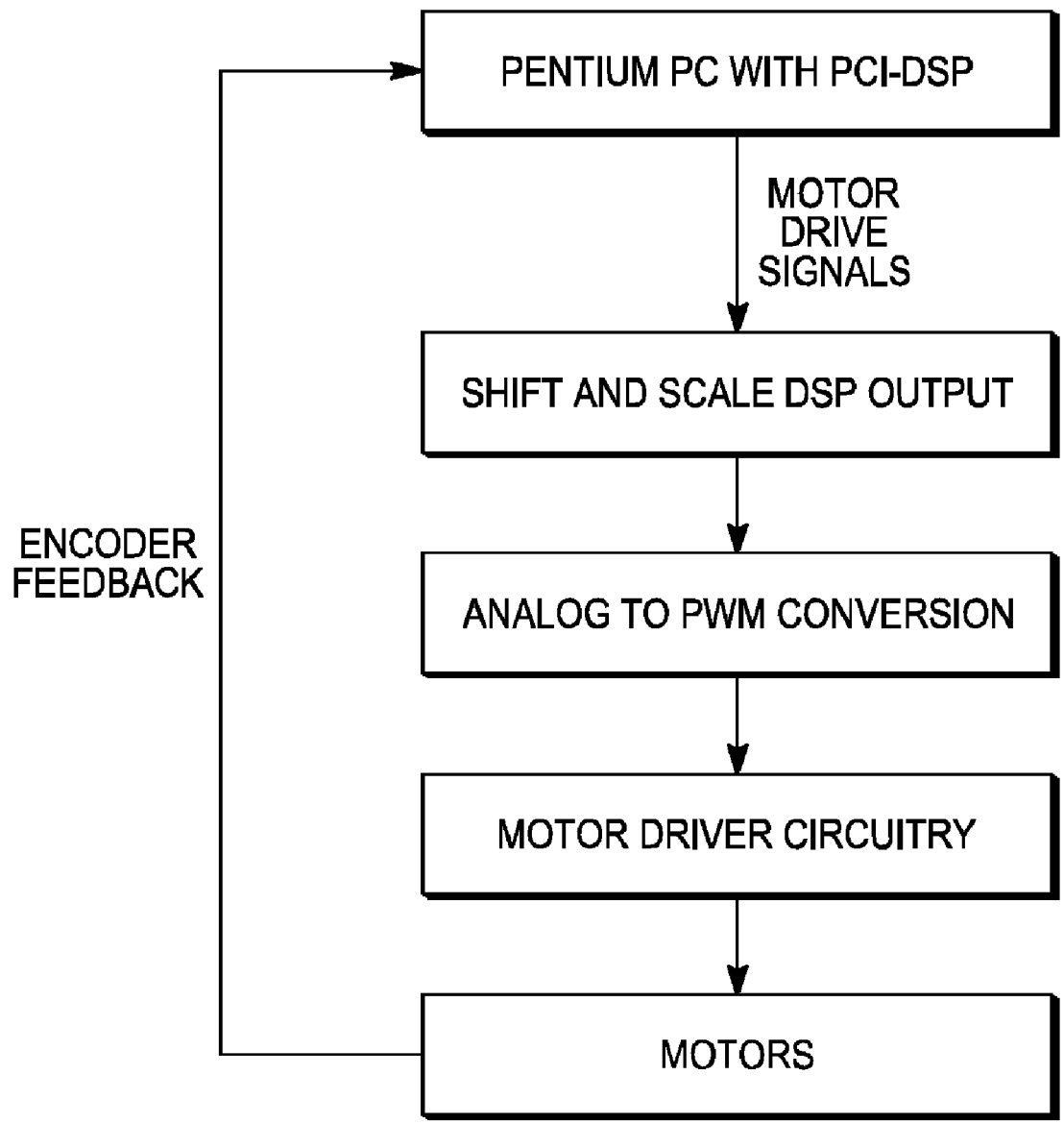
FIG. 8 is a block diagram of the electronics and control system used in one embodiment of a manipulator arm.

In one embodiment as depicted in FIG. 8, the electronics and control for the arm consists of four major sections: PC with a MEI DSP motor driver PCI card, an analog circuit to shift and scale the output voltage from the MEI card, a microcontroller to convert each axis' analog voltage to a PWM signal, and an H-Bridge ICS to drive the motors. This embodiment is described in further detail in U.S. Pat. No. 7,199,545.

In one embodiment, the manipulator is a biopsy forceps or grasper. According to one aspect, the manipulator includes a biopsy forceps or graspers at one end of an arm.

In another embodiment, the manipulator of the present invention includes an actuation mechanism that generates forces required for operating the manipulator. For example, according to one embodiment in which the manipulator is a biopsy forceps or graspers, the manipulator also has an actuation mechanism that generates sufficient force to allow the forceps or graspers to cut/obtain a biopsy sample. According to one embodiment, the actuation mechanism generates a drawbar force of magnitude greater than 0.6 N. Alternatively, the actuation mechanism generates any amount of force sufficient to obtain a biopsy sample. In a further alternative, the actuation mechanism generates a sufficient force to operate any type of manipulator, such as a clamp, stapler, cutter, cauterizer, burner, etc.

Figure 9A:
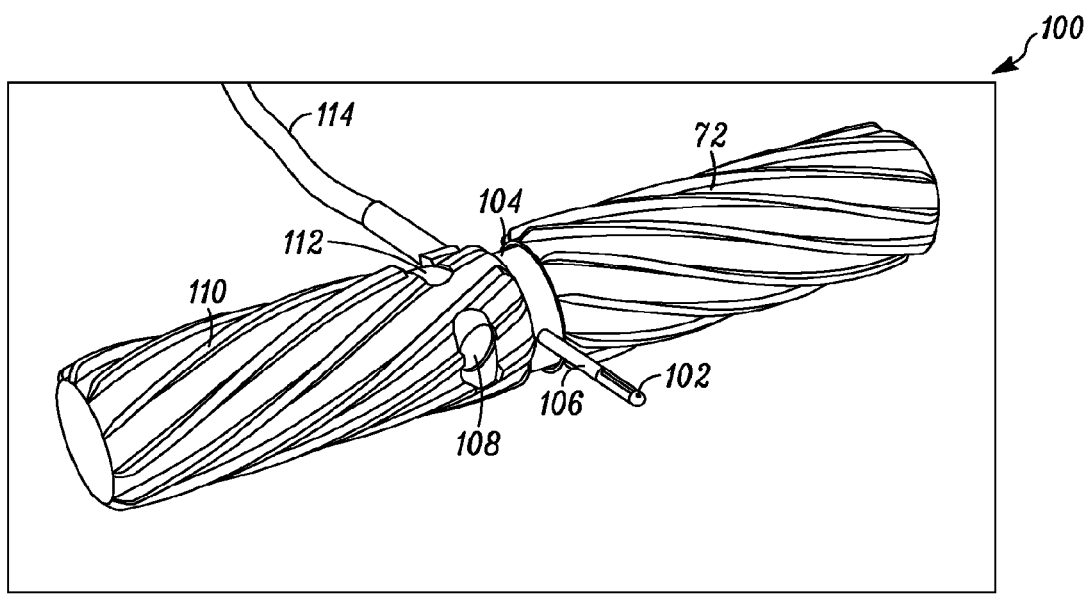
FIG. 9A is a perspective view of a mobile robotic device, according to another embodiment.

FIG. 9A depicts a robotic device 100 having a biopsy tool 102. The cylindrical robotic device 100 has a cylindrical body 104 having an appendage or arm 106 with a biopsy forceps 102 at one end of the arm that is used for sampling tissue. According to one embodiment, the robot's grasper 102 can open to 120 degrees. In a further alternative, the forceps 102 can have any known configuration.

In one embodiment, the body 104 also contains an imaging component (not shown), camera lens 108, motor and video control boards (not shown), and actuation motor (not shown) and a mechanism for camera adjustable-focus (not shown). In this embodiment, the imaging component and lens 108 are offset to the side to allow space for the biopsy grasper 102. The wheel 110 on the camera side has slots 112 machined in it to allow for space for the camera lens 108 to see the abdominal environment and the biopsy grasper 102. Alternatively, the camera and lens 108 are disposed anywhere on the robotic device 100 such that the camera can be used to view the surgical area and/or the biopsy grasper 102 during use. The device 100 a wired connection component 114 that is connected to an external component (not shown).

Figure 9B:
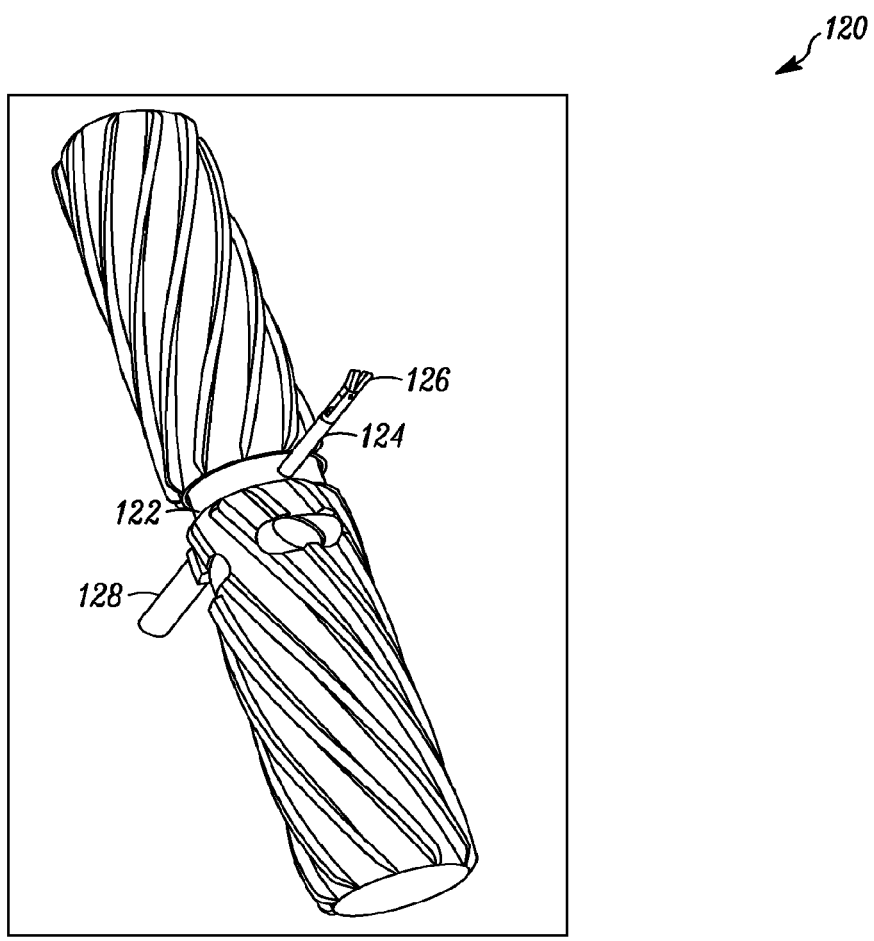
FIG. 9B is a perspective view of a mobile robotic device, according to yet another embodiment.

FIG. 9B depicts a mobile robotic device 120, according to an alternative embodiment. In this embodiment, the device 120 is wireless. That is, the device 120 has no wired connection component physically connecting the device 120 to an external component positioned outside the patient's body. In the configuration of FIG. 9B, the device 120 has a configuration similar to the wired device in FIG. 9A. That is, the device 120 has a cylindrical body 122 and an arm 124 having a biopsy tool 126. Further, the device 120 can also have other components similar to those described above with respect to the embodiment in FIG. 9A. In one alternative implementation, the device 120 also has a "tail" 128, described in further detail above, connected to the body 122.

In use, a robotic device with a camera and a biopsy tool such as the devices depicted in FIGS. 9A and 9B can be used to obtain a biopsy sample. The device can be inserted into the body, such as through a standard trocar or using any of the natural orifice procedures described herein. The user can control the device using visual feedback from the on-board camera. This mobility allows the robot to move to the area of interest to sample specific tissues. The biopsy tool can then be actuated to obtain a tissue sample. In a further embodiment, the biopsy forceps provide a clamp capable of clamping shut a severed artery.

In an alternative embodiment, the manipulator is a drug delivery component. That is, according to one implementation, robotic devices disclosed herein can have a drug delivery component or system that delivers an agent to an animal, including a human. In one embodiment, the agent is a hemostatic agent. Alternatively, the agent can be any deliverable composition for delivery to an animal, including a human.

Figure 10:
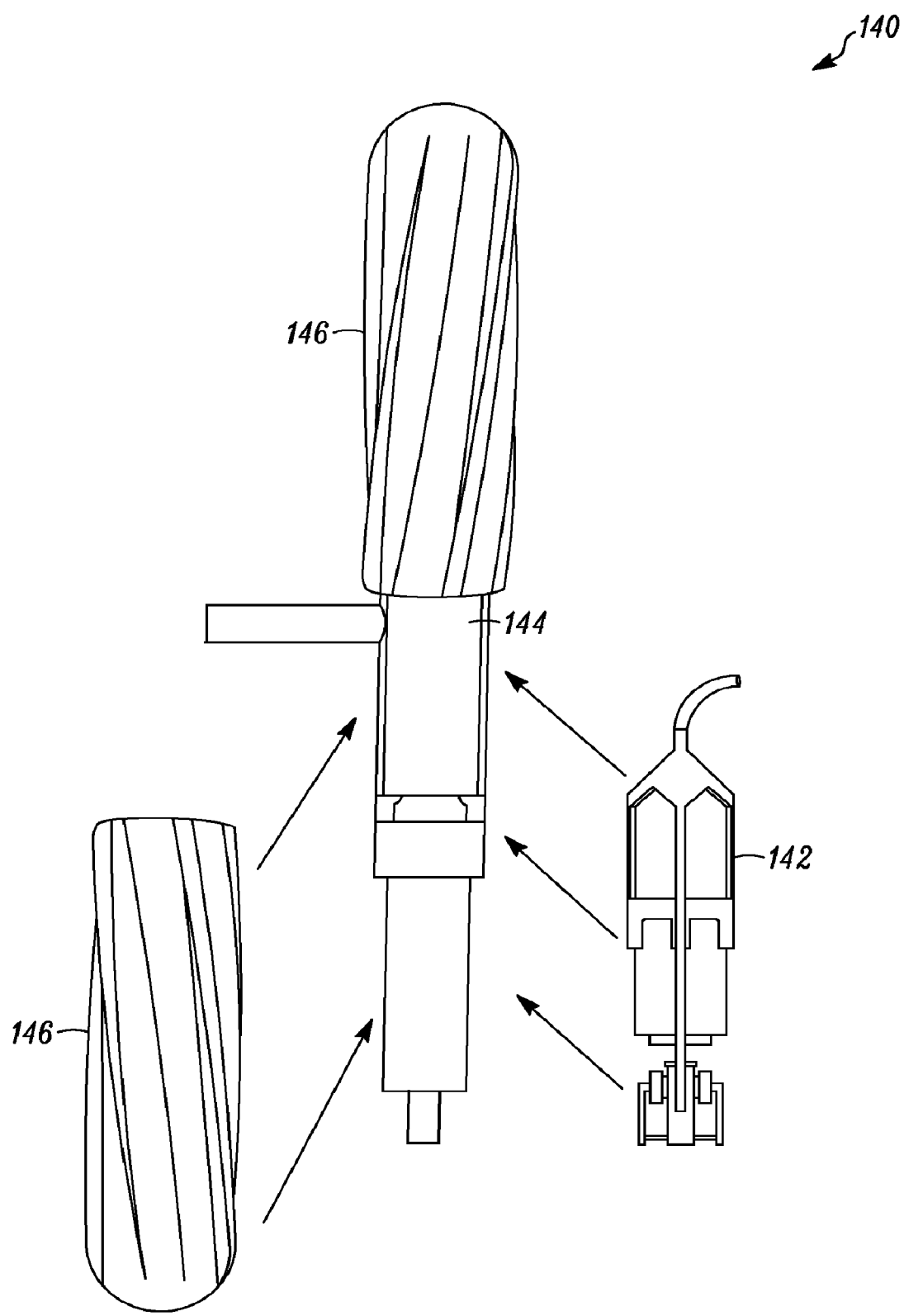
FIG. 10 is a plan view of a mobile robotic device having a drug delivery component, according to another embodiment.

FIG. 10 depicts a robotic device 140 having an agent delivery system 142, according to one embodiment. In this embodiment, the delivery system 142 is disposed within the cylindrical body 144 and two wheels 146 are rotatably disposed over the cylindrical body 144. The device 140 can also have an imaging component (not shown). Alternatively, the device need not have an imaging component.

Figure 11A:
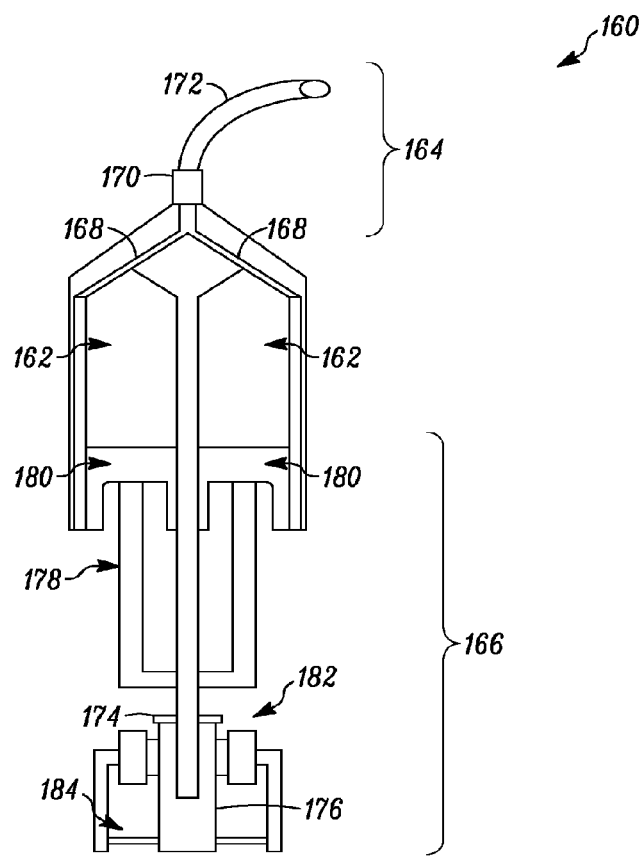
FIGS. 11A and B are schematic depictions of a drug delivery component that can be integrated into a mobile robotic device, according to one embodiment.

FIG. 11A depicts an agent delivery component 160, according to one embodiment. The delivery component 160 in this embodiment is an agent storage and dispensing system. In one embodiment, the agent is a hemostatic agent. The system has dual reservoirs 162 that can contain the agent, a mixing and discharge component 164, and an actuation component 166. According to one embodiment, the mixing and discharge component 164 has two delivery tubes 168, a manifold 170 and a cannula 172. Alternatively, the mixing and discharge component 164 is actually two separate components: a mixing component and a discharge component. In one implementation, the actuation component 166 has a crank wheel 174, a catch lever 176, and a ratcheting linkage 178 coupling the crank wheel 174 to plungers 180 disposed within the reservoirs 162.

In one embodiment, the dual reservoirs 162 of FIG. 11A are configured to store and isolate two agents or agent components. In one implementation, the reservoirs 162 are similar to those used in standard dual syringe injection systems. According to one embodiment, the two components are two separate components of the hemostatic agent. That is, as is understood in the art, many hemostatic agents are comprised of two components that must be preserved separately to prevent premature coagulation prior to application. In this embodiment, the storage and dispensing system has dual reservoirs system configured to store and isolate the two components until they are dispensed. Alternatively, the agent is a single component hemostat that does not need to be combined with another component, and the same agent is placed in both reservoirs. In a further alternative, the system has a single reservoir or container for any agent that need not be combined with another. In yet another alternative, the system can have more than two reservoirs.

Figure 11B:
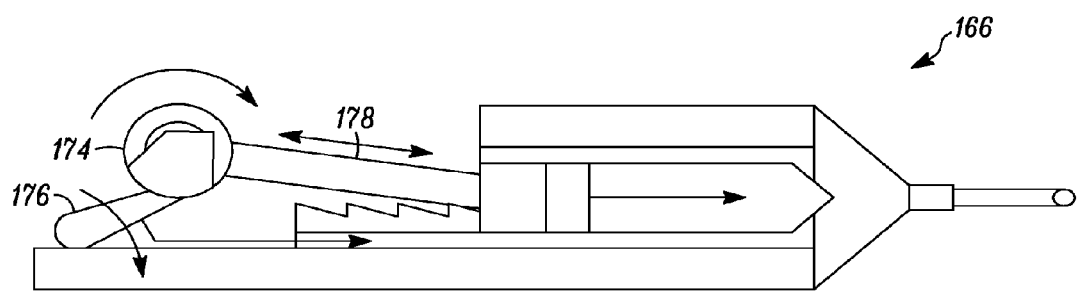

FIG. 11B, along with FIG. 11A, provides an additional perspective relating to the actuation component 166. The actuation component 166 has pre-loaded torsional springs 182 that are pre-wound and rigidly attached to the crank wheel 174. In addition, the lever 176, according to one embodiment, is also attached to torsion springs 184. When the lever 176 is released, the stored mechanical energy in the springs 182 causes the crank wheel 174 to rotate. The off-center attachment point of the ratcheting linkage 178 to the crank wheel 174 converts rotational displacement of the wheel 174 into linear displacement of the plungers 180.

According to one embodiment, the spring-loaded catch lever 176 is a shape memory alloy and is actuated with a SMA wire trigger. SMA wires are made of a nickel-titanium alloy that is easily stretched at room temperature. However, as the wires are heated by passing an electric current through them, they shorten in length and exert a force that is greater than the force required to stretch them. In one embodiment, the wires shorten in length by up to approximately 8% and exert approximately 5 times the force required to stretch them.

Figure 12:
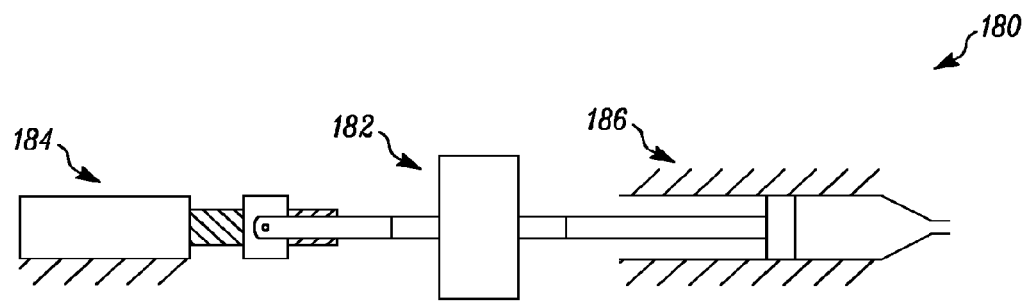
FIG. 12 is a schematic depiction of a test jig for measuring the applied force required to move a plunger in a drug delivery component, according to one embodiment.

A further alternative embodiment of the actuator mechanism is depicted in FIG. 12 and is described in further detail below in Example 6. That mechanism uses a permanent magnet direct current motor as the force actuator.

Alternatively, the actuator mechanism can be any known device for providing for linear displacement of the reservoir plungers 180 that dispense the agent. According to one implementation, the actuator ensures uniform delivery of the agent from the storage reservoir(s).

Figure 13A:
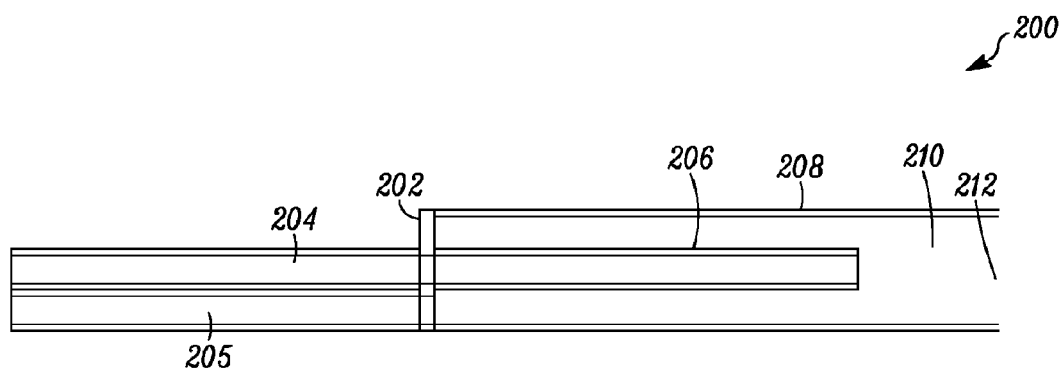
FIGS. 13A and B are schematic depictions of the profile of a drug delivery component, according to one embodiment.

FIG. 13A depicts a mixing component 200, according to one embodiment. The system 200 includes a manifold 202 and two delivery components or tubes 204, 205. Projecting from the end of the manifold 202 is a length of tubing 206 that contains one of the fluid flows and fits inside a larger diameter cannula 208. The system 200 has a mixing site 210 and a discharge site 212. The mixing component is a device for mixing and delivering at least two fluid components simultaneously through a single cannula. In implementations in which the agent is a hemostatic agent requiring two compounds, the mixing component thoroughly mixes the two components as necessary to promote optimal coagulation. In one embodiment, a mixing system ensures that the two components come into contact near the exit port in such a way as to promote efficient mixing and that all reactive material is ejected to prevent clogging of the cannula.

Figure 13B:
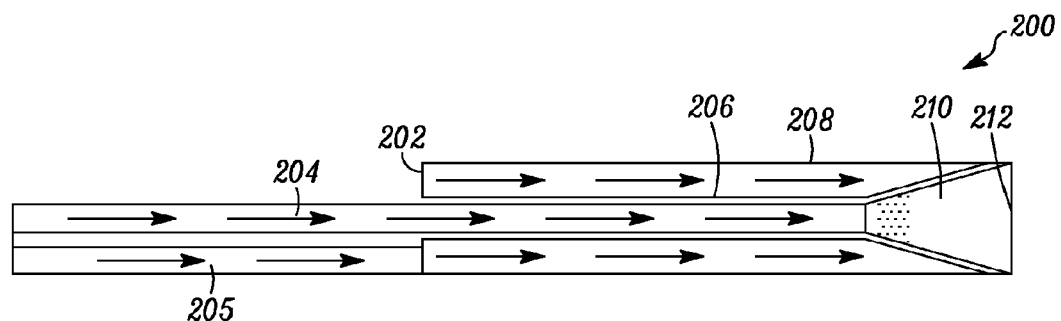

FIG. 13B depicts the flow of agents in the mixing component 200 of FIG. 13A. In this embodiment, the fluids contained in the two storage reservoirs (not shown) are delivered simultaneously to the manifold 202 through the delivery tubes 204, 205. The fluid flow in delivery tube 205 exits the manifold 202 and is forced around the tubing 206 through the length of the cannula 208. The fluids mix in the mixing site 210 near the discharge site 212, and any reactive material is ejected from the larger diameter cannula 208 at the discharge site 212. According to one embodiment, the point at which mixing commences and, hence, the time available prior to delivery, can be adjusted by changing the diameters and lengths of the tubing and cannula. Further, spirals or other features can be incorporated along the inside surface of the cannula 208 to enhance the mixing efficiency of this system.

Alternatively, the mixing component is any known component for mixing two agents, including, but not limited to, hemostatic agents, that can implemented with one or more of the robotic devices described herein.

In accordance with one aspect, the reservoir or reservoirs have at least one externally accessible loading port configured to allow for loading, injecting, or otherwise placing the agent or components into the reservoir. The loading port is a standard rubber stopper and seal commonly used for vaccine vials. Such a rubber stopper and seal facilitates transfer of any agent using a standard syringe. Alternatively, the loading port is any known type of loading port of any known configuration. According to one embodiment, such a loading port is useful for known agents that must be reconstituted shortly before use, such as on-site reconstitution. As such, the loading port or ports accommodate the need for on-site loading of the compounds.

According to one aspect, any robotic device embodiment described herein is connected to an external controller via a connection component. According to one embodiment, the connection component is a wire, cord, or other physical flexible coupling. For purposes of this application, the physical or "wired" connection component is also referred to as "tethered" or "a tether." The flexible connection component can be any component that is coupled at one end to the robotic device and is flexible, pliable, or otherwise capable of being easily formed or manipulated into different shapes or configurations. According to one embodiment, the connection component includes one or more wires or cords or any other type of component operably coupled at the second end to an external unit or device. The component in this embodiment is configured to transmit or convey power and/or data, or anything else necessary or useful for operation of the device between the robotic unit and the external unit or device. In a further alternative, the connection component comprises at least two wires or cords or other such components, each of which are connected to a separate external unit (which, in one example, are a power source and a data transmission and receiver unit as described below).

Alternatively, the connection component is a wireless connection component. That is, the robotic device communicates wirelessly with a controller or any other external component. The wireless coupling is also referred to herein as "untethered." An "untethered device" or "wireless device" is intended for purposes of this application to mean any device that is fully enclosed within the body such that no portion of the device is external to the body for at least a portion of the surgical procedure or, alternatively, any device that operates within the body while the device is not physically connected to any external object for at least a portion of the surgical procedure. In one embodiment, an untethered robotic device transmits and receives data wirelessly, including data required for controlling the device. In this embodiment, the robotic device has an internal power supply, along with a receiver and transmitter for wireless connection.

The receiver and transmitter used with a wireless robotic device as described herein can be any known receiver and transmitter. For example, any known receiver and/or transmitter used in remote vehicle locking devices, remote controls, mobile phones.

In one embodiment, the data or information transmitted to the robotic device could include user command signals for controlling the device, such as signals to move or otherwise operate various components. According to one implementation, the data or information transmitted from the robotic device to an external component/unit could include data from the imaging component or any sensors. Alternatively, the data or information transmitted between the device and any external component/unit can be any data or information that may be useful in the operation of the device.

According to another implementation, any robotic device embodiment described herein is connected via a connection component not only to the external controller, but also to one or more other robotic devices, such devices being either as described herein or otherwise known in the art. That is, according to one embodiment, two or more robotic devices can be operably coupled to each other as well as an external unit or device. According to one embodiment in which there are two robotic devices, the two devices are operably coupled to each other and an external unit or device by a flexible connection component. That is, the two devices are operably coupled to each other by a flexible connection component that is coupled to each device and each device is also operably coupled to an external unit or device by a flexible connection component. In one embodiment, there are three separate flexible connection components: (1) a connection component connecting the two robotic devices, (2) a connection component connecting one of the robotic devices to the external unit, and (3) a connection component connecting the other of the robotic devices to the external unit. Alternatively, one connection component is operably coupled to both devices and the external unit. In a further alternative, any number of connection components can be used in any configuration to provide for connection of two robotic devices to each other and an external unit.

Alternatively, the two or more robotic devices are operably coupled to each other as well as an external unit or device in an untethered fashion. That is, the robotic devices are operably coupled to each other and an external unit or device in a fashion such that they are not physically connected. In one embodiment, the devices and the external unit are operably coupled wirelessly.

In one aspect, any robotic device described herein has a drive component. The "drive component," as defined herein, is any component configured to provide motive force such that the robotic device can move from one place to another or some component or piece of the robotic device can move, including any such component as described herein. The drive component is also referred to herein as an "actuator." In one implementation, the drive component is a motor.

The actuator can be chosen from any number of different actuators. For example, one actuator that can be incorporated into many, if not all, of the robotic devices described herein, is a brushless direct current motor, such as, for example, model no. SBLO4-0829 with gearhead PG04-337 (available from Namiki Precision of California, which is located in Belmont, Calif.). According to one embodiment, this motor requires external connection, which is generally provided by a circuit supplied by the manufacturer. In another implementation, the motor is model no. SBL02-06H1 with gearhead PG02-337, also available from Namiki.

Alternatively, any brushless direct current motor can be used. In a further alternative, another motor that can be used to operate various components of a robotic device, such as a manipulator, is a permanent magnet DC motor made by MicroMO™ Electronics, Inc. (located in Clearwater, Fla.). In yet another alternative, any known permanent magnet DC motors can be used with the robotic devices described herein.

The motor runs on a nominal 3 V and can provide 10.6 [mNm] stall torque at 80 rpm. This motor provides a design factor of 4 for the robot on a 75-degree slope (if frictional force is sufficient to prevent sliding).

In addition, other actuators that can be used with the robotic devices described herein include shape memory alloys, piezoelectric-based actuators, pneumatic motors, hydraulic motors, or the like. Alternatively, the robotic devices described herein can use any type of compatible actuator.

According to one embodiment, the actuator can have a control component, also referred to as a "control board." The control board can have a potentiometer that controls the speed of the motor relationship between the terminals that created the voltage divider. According to one embodiment, the control board can also control the direction of the motor's rotation.

In accordance with one implementation, any robotic device as described herein can have an external control component, also referred to herein as a "controller." That is, at least some of the devices herein are operated by a controller that is positioned at a location external to the animal or human.

In one embodiment, the external control component transmits and/or receives data. In one example, the unit is a controller unit configured to control the operation of the robotic device by transmitting data such as electronic operational instructions via the connection component, wherein the connection component can be a wired or physical component or a wireless component. The data transmitted or conveyed by the connection component can also include, but is not limited to, electronic data collected by the device such as electronic photographs or biopsy data or any other type of data collected by the device. Alternatively, the external unit is any component, device, or unit that can be used to transmit or receive data.

According to one embodiment, the external component is a joystick controller. In another example, the external component is any component, device, or unit that can be used to control or operate the robotic device, such as a touch screen, a keyboard, a steering wheel, a button or set of buttons, or any other known control device. Further, the external component can also be a controller that is actuated by voice, such as a voice activation component. Further, a controller may be purchased from commercial sources, constructed de novo, or commercially available controllers may be customized to control any robotic device or any robotic device components disclosed herein.

In one example, the controller includes the "thumb sticks" from a Playstation™ Dual-Shock controller. In this example, the Playstation™ controller had two analog thumb sticks, each with two degrees of freedom. This allows the operator to move the thumbsticks a finite amount in an XY coordinate plane such that pushing the stick forward a little yields a different output than pushing the stick forward a great deal. That is, the thumb sticks provide speed control such that movement can be sped up or slowed down based on the amount that the stick is pushed in the corresponding direction.

According to one embodiment, the connections between the controller and the robotic device are configured such that each wheel is controlled by a separate joystick.

In another example, the controller is a directional pad similar to the directional pad on an original Nintendo™ game system. The pad resembles a + sign and has four discrete directions.

In use, the controller can be used to control the movement of the robotic device and further to control the operation of any components of the device such as a sensor component, a manipulator component, or any other such component. For example, one embodiment of the controller controls the wheels, the focus adjustment of the camera, and further controls the biopsy tool.

In accordance with one embodiment, the control component also serves as a power source for the robotic device.

In accordance with one embodiment, a mobile robotic device is coupled to an image display component. Signal from the camera is transmitted in any format (e.g., NTSC, digital, PAL, etc.) to the image display component. According to one embodiment, the signal is a video signal or a still image signal. In one embodiment, the image display component is a video display that can be viewed by the operator. Alternatively, the image display component is a still image display. In a further alternative, the image display component displays video and still images. In one embodiment, the image display component is a standard video monitor. Those of ordinary skill in the art recognize that a signal from a camera can be processed to produce a display signal for many different types of display devices, including televisions configured to display an NTSC signal, televisions configured to display a PAL signal, cathode ray tube based computer monitors, LCD monitors, and plasma displays. In a further embodiment, the image display component is any known image display component capable of displaying the images collected by a camera that can be used with any of the robotic devices described herein.

In one embodiment, the image display component is a component of the controller.

A robotic device as described herein, according to one implementation, has a power source or power supply. According to one embodiment, the power source is integrated into the body of robotic device. In this embodiment, the power source can be one or more batteries. The battery can be an alkaline, lithium, nickel-cadmium, or any other type of battery known in the art.

Alternatively, the power source is positioned in a location external to the body of the patient. In this embodiment, the connection component operably coupled to the power source and the robotic device transmits or conveys power between the power source and the robotic device. For example, the external power source according to one embodiment is an electrical power source such as a battery or any other source of electricity. In this example, the electricity is conveyed from the battery to the robotic device via the connection component, which is any known wire or cord configured to convey electricity, and thereby supplies power to the robotic device, including the motor of the robotic device. In one example, the power source is integrated into the control component or is operably coupled to the control component.

According to one embodiment, the power source can be any battery as described above. Alternatively, the power source can be magnetic induction, piezoelectrics, nuclear, fluid dynamic, solar or any other known power source that can be used to supply power to any robotic device described herein.

Certain embodiments of robotic devices disclosed herein relate to fixed base robots. As discussed above, a "fixed base robotic device" is any robotic device that has no propelled transport component or is positioned manually by a user. Such a device is also referred to herein as a "stationary" robotic device. In one embodiment, a fixed base robot has a camera and is positioned manually by the user to provide visual feedback or a visual overview of the target area. A fixed base robotic camera device according to one implementation facilitates the application of laparoscopy and other surgical techniques by providing a remote-control camera robot to provide visual feedback during a surgical procedure, thereby minimizing incisions and patient risk.

Figure 14:
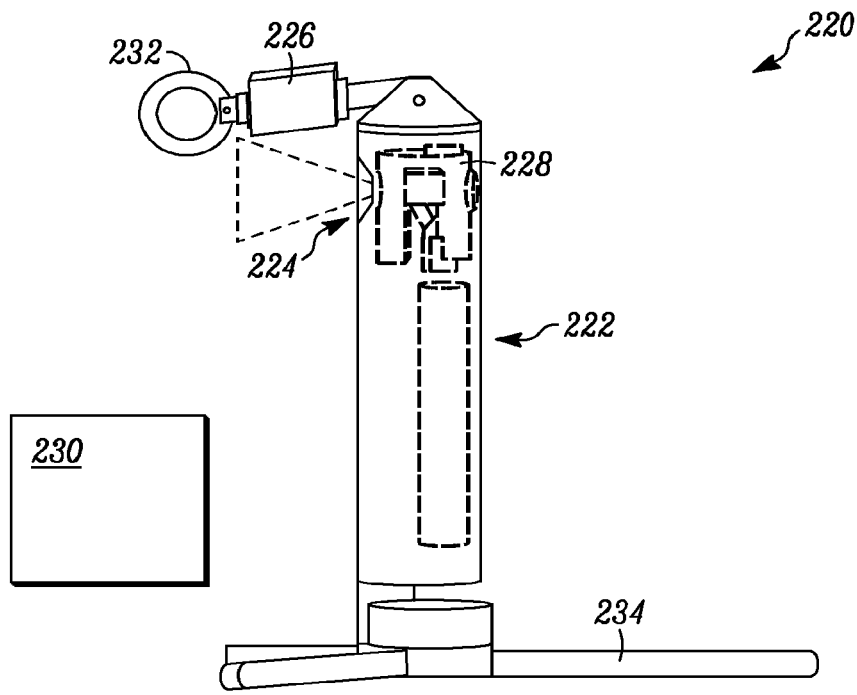
FIG. 14 is a side view of a stationary or fixed base robotic device in the deployed configuration, according to one embodiment.

FIG. 14 depicts a robotic imaging device 220, according to one embodiment. The device 220 has a main body 222 with an imaging component 224 disposed therein, an adjustable-focus component 228, and a support component 234 for supporting the body 222 inside an open space (e.g., a body cavity). In one embodiment, the device 220 further contains a light component 226 for illumination, a handle 232, and a controller 230 for controlling various components of the device 220 such as the panning or tilting components (discussed below) or the adjustable-focus component 228. According to one embodiment, the device 220 is sized for use with standard laparoscopic tools.

In one embodiment, the device 220 is made of a biocompatible material capable of being easily sterilized. According to one embodiment, the materials can include, but are not limited to, sterilizable plastics and/or metals. Alternatively, the device 220 can be made of any material that can be used in surgical procedures.

The body 222 can take on many different configurations, such as cylindrical or spherical shapes so as to be compatible with laparoscopic tools known currently in the art. However, as with the other components, the body 222 configuration is not limited to that exemplified herein. In general, the only constraints on the shape of the body are that the body be able to incorporate at least one of the components described herein.

The handle 232, according to one embodiment as depicted in FIG. 14, is a retractable or otherwise movable handle 232 formed into the shape of a ring or loop. Alternatively, the handle can be rigid or unmovable. In a further alternative, the handle 232 is any component in any configuration that allows for easy repositioning or manipulation of the device 220. In one aspect, the handle 232 is provided to allow for a grasping tool or other type of tool to attach to the device 220 via the handle 232 and thereby reposition or otherwise manipulate the device 220 in the patient. That is, the device 220 can be repositioned using the handle 232 to provide a different field of view for the imaging component 224, thereby providing a new viewpoint for the user. Thus, the movement of the device 220 enables the imaging component 224 to obtain an image of at least a portion of the surgical area from a plurality of different angles without constraint by the entry incision.

The light component 226, according to one embodiment, is configured to light the area to be viewed, also referred to as the "field of view." In one implementation, the light component 226 is proximate to the imaging component to provide constant or variable illumination for the camera. Alternatively, the light component 226 is associated with the handle 232 as depicted in FIG. 14. In such an embodiment, the light source 226 illuminates the field of view as well as the handle 232, thereby facilitating easy capture or grasping of the handle 232 by a tool.

In one example, the lighting component 226 is an LED light. Alternatively, an exemplary light source is two 5 mm LEDs. In a further alternative, the lighting component 226 can be any suitable illumination source.

In one implementation, the imaging component 224 depicted in FIG. 14 can be a camera or any other imaging device. In certain embodiments, the imaging component can be any imaging component as described above with respect to mobile robotic devices. Regardless, the camera can be any known imaging component that can be used with any of the fixed base robotic devices contemplated herein. In one embodiment, the imaging component is a stereo camera that creates a three-dimensional image.

The imaging component can help to increase or improve the view of the area of interest (such as, for example, the area where a procedure will be performed) for the user. According to one embodiment, the imaging component provides real-time video to the user. Alternatively, the imaging component can be any imaging component as described above with respect to the mobile robotic devices.

Figure 15:
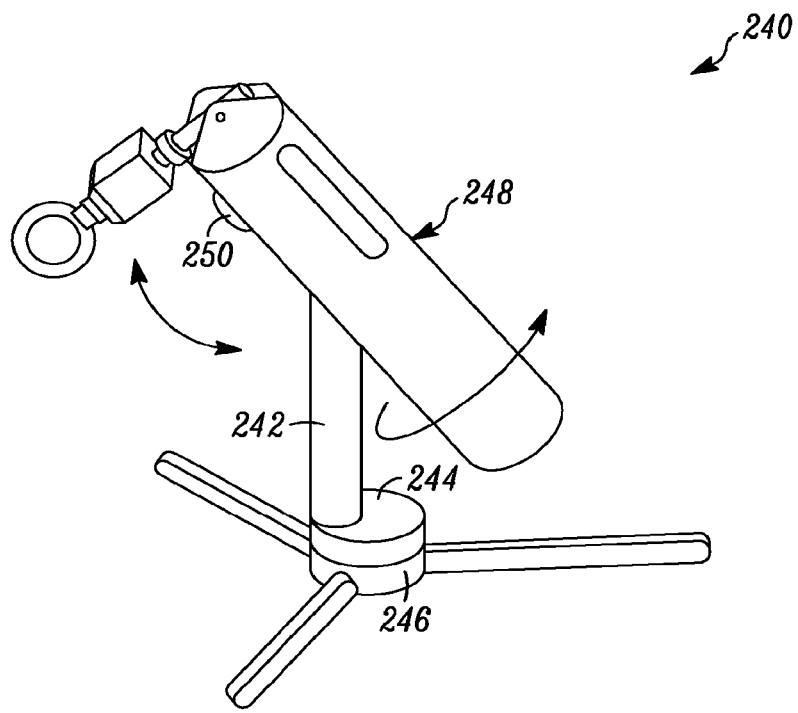
FIG. 15 is a side view of a fixed base robotic device in the deployed configuration, according to one embodiment.

FIG. 15 depicts another embodiment of a fixed base robotic camera device 240. The device 240 has a tilting component 242 and a panning component 244, 246. The panning component 244, 246 has a small ball bearing structure 244 that is attached to a base 246, thereby allowing freedom of rotation. That is, the structure 244 is rotatable with respect to the base 246. In certain embodiments, the panning and tilting components provide rotation about two independent axes, thereby allowing the surgeon more in-depth visualization of the abdominal cavity for surgical planning and procedures.

In accordance with one implementation, the tilting component 242 is pivotally coupled to the body 248 via a pin (not shown). Alternatively, the tilting component can be a standard ratchet mechanism or any other type of suitable component known in the art. According to one embodiment, the tilting component 242 can tilt up to about 45 degrees from vertical (i.e., a range of about 90 degrees). Alternatively, the tilting component 242 can tilt any amount ranging from about 0 degrees to about 360 degrees from vertical, or the tilting component 242 can configured to rotate beyond 360 degrees or can rotate multiple times. In certain embodiments such as the embodiment depicted in FIG. 2, the tilting component 242 is a separate component associated with, but independent of, the body 248. Alternatively, the tilting component is incorporated into the body 248 or into the camera component 250.

The panning component 244, 246, according to one embodiment, has the two components 244, 246 that rotate with respect to each other as described above with respect to FIG. 2. Alternatively, the panning component can be any suitable component known in the art. According ton one implementation, the panning component 244, 246 provides for panning the device up to and including or beyond 360 degrees. Alternatively, the panning component 244, 246 provides for panning any amount ranging from about 180 degrees to about 360 degrees. In a further alternative, the panning component 244, 246 provides for panning any amount ranging from about 0 degrees to about 360 degrees. In certain embodiments such as the embodiment depicted in FIG. 2, the panning component 244, 246 is a separate component associated with, but independent of, the body 248. Alternatively, the panning component is incorporated into the body 248 or into the camera component 250.

In one aspect, any fixed base robotic device described herein has a drive component (not shown). In accordance with certain embodiments, the fixed base robotic device can have more than one drive component. For example, in one embodiment, a fixed base robotic device has a motor for actuating the panning component and another motor for actuating the tilting component. Such motors can be housed in the body component and/or the support component. In one example, the actuator or actuators are independent permanent magnet DC motors available from MicroMo™ Electronics, Inc. in Clearwater, Fla. Other suitable actuators include shape memory alloys, piezoelectric-based actuators, pneumatic motors, hydraulic motors, or the like. Alternatively, the drive component can be any drive component as described in detail above with respect to mobile robotic devices. In a further alternative embodiment, the panning and tilting components can be actuated manually.

In one embodiment, the actuator is coupled to a standard rotary-to-translatory coupling such as a lead screw, a gear, or a pulley. In this fashion, the force created by the actuator is translated with the rotary-to translatory coupling.

Moreover, it is also contemplated that the body or camera in certain embodiments could be capable of a side-to-side motion (e.g., yaw).

Various embodiments of fixed base robotic devices have an adjustable-focus component. For example, one embodiment of an adjustable-focus component 60 that can incorporated into various embodiments of the fixed base robotic devices described herein is depicted in FIG. 4 and described in detail above. Alternatively, a variety of adjustable-focus means or mechanisms are known in the art and suitable for active or passive actuation of focusing an imaging component. For example, one design employs the use of a motor and a lead screw. The motor turns a turn-table that is attached to a lead screw. A mating nut is attached to the imager. As the lead screw turns the imager translates toward and away from the lens that is mounted to the body of the robot.

According to one embodiment, the imaging component can have a lens cleaning component. For example, the lens cleaning component can be a wiper blade or sacrificial film compose of multiple layers for maintaining a clear view of the target environment. In a further embodiment, the lens cleaning component can be any known mechanism or component for cleaning a camera lens.

Figure 16:
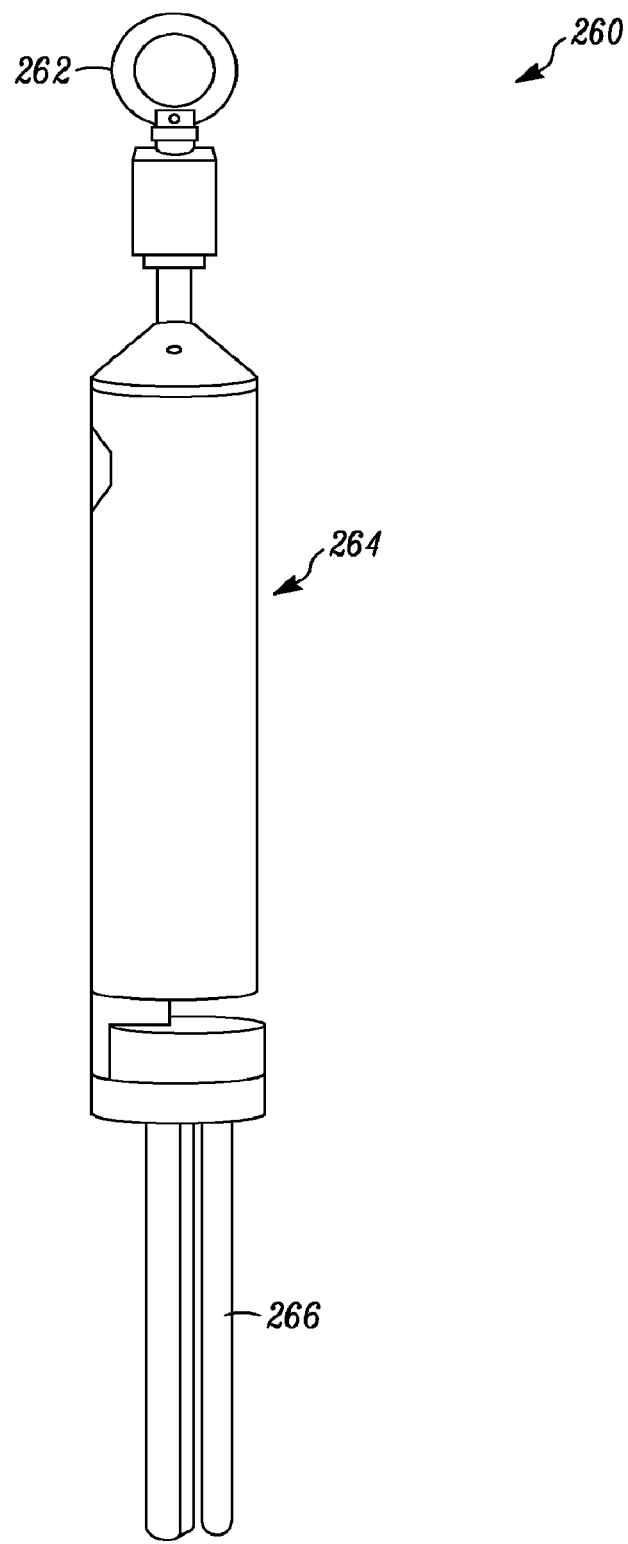
FIG. 16 is a side view of a fixed base robotic device in the collapsed configuration, according to one embodiment.

Certain embodiments of the fixed base robotic devices, such as the embodiment depicted in FIG. 16, are designed to collapse or otherwise be reconfigurable into a smaller profile. For example, according to one embodiment, the device 260 is configurable to fit inside a trocar for insertion into and retraction from an animal's body. In the collapsed position as depicted, handle 262 is coaxial with robot body 264 of device 260. Upon introduction into an open space, handle 262 can be deployed manually, mechanically actuated, or spring loaded as exemplified herein to rotate down 90 degrees to a position similar to that shown in FIGS. 1 and 2. In one embodiment, such passive actuation is achieved with torsion springs (not shown) mounted to the handle at the axis of rotation.

The support component 266, as depicted in FIG. 16, is a set of one or more legs 266 that are moveable between a collapsed and a operational or deployed position. For example, in FIG. 16, the legs in the collapsed position are coaxial with body 264 of the device 260. The support component 266 can be deployed manually, or by mechanical actuation, or as by spring loading as exemplified herein (e.g., with torsion springs) to rotate up 90 degrees to a configuration similar to that shown in the FIGS. 1 and 2. According to one implementation, the support component can be, but is not limited to, legs, feet, skis or wheels, or any other component that can facilitate positioning, weight distribution, and/or stability of a fixed base robotic device of any configuration described herein within a patient's body. Alternatively, the support component can be equipped with magnets such that the device could be suspended within the open space by positioning a magnet external of the open space.

According to one aspect, any fixed base robotic device embodiment described herein is connected to an external controller via a connection component. According to one embodiment, the connection component is any wired or flexible connection component embodiment or configuration as described above with respect to mobile robotic devices. Alternatively, the connection component is a wireless connection component according to any embodiment or configuration as described above with respect to mobile robotic devices. The receiver and transmitter used with a wireless robotic device as described herein can be any known receiver and transmitter, as also described above. According to another implementation described in additional detail above with respect to the mobile devices, any fixed base robotic device embodiment described herein can be connected via a (wired or wireless) connection component not only to the external controller, but also to one or more other robotic devices of any type or configuration, such devices being either as described herein or otherwise known in the art.

In one embodiment, the data or information transmitted to the robotic device could include user command signals for controlling the device, such as signals to move or otherwise operate various components. According to one implementation, the data or information transmitted from the robotic device to an external component/unit could include data from the imaging component or any sensors. Alternatively, the data or information transmitted between the device and any external component/unit can be any data or information that may be useful in the operation of the device.

In accordance with one implementation, any fixed base robotic device as described herein can have an external control component according to any embodiment as described above with respect to the mobile robotic devices. That is, at least some of the fixed base devices herein are operated by a controller that is positioned at a location external to the animal or human. In one embodiment, the external control component transmits and/or receives data. In one example, the unit is a controller unit configured to control the operation of the robotic device by transmitting data such as electronic operational instructions via the connection component, wherein the connection component can be a wired or physical component or a wireless component. Alternatively, the external unit is any component, device, or unit that can be used to transmit or receive data.

In use, the controller can be used to control the movement or operation of any components of the device such as the camera component, a sensor component, or any other component. For example, one embodiment of the controller controls the focus adjustment of the camera, and further controls the panning and/or tilting functions of the device.

According to one embodiment, the control component is configured to control the operation of the image sensor, the panning component, and the tilting component. In one embodiment, the control component transmits signals containing operational instructions relating to controlling each of those components, such as, for example, signals containing operational instructions to the image sensor relating to image quality adjustment, etc.

In accordance with one embodiment, the control component also serves as a power source for the robotic device.

According to one implementation, the fixed base robotic device is coupled to an image display component. The image display component can be any image display component as described above with respect to the mobile robotic devices.

A fixed base robotic device as described herein, according to one implementation, has a power source or power supply. According to one embodiment, the power source is any power source having any configuration as described above with respect to the mobile robotic devices. According to various embodiments, power can be provided by an external tether or an internal power source. When the device is wireless (that is, the connection component is wireless), an internal power supply can be used. Various implementations of the fixed base robotic devices can use alkaline, lithium, nickel-cadmium, or any other type of battery known in the art. Alternatively, the power source can be magnetic induction, piezoelectrics, fluid dynamics, solar power, or any other known power source. In a further alternative, the power source is a power unit positioned within the patient's body. In this embodiment, the power unit can be used to supply power not only to one or more robotic camera devices, but can also to any other surgical robotic devices.

In one embodiment, the fixed base robotic device has one or more sensor components. In various embodiments, such sensor components include any of the sensor components as described above with respect to the mobile robotic devices.

According to one embodiment, the fixed base robotic device has one or more operational components. In various embodiments, such operational components include any of the operational components as described above with respect to mobile robotic devices. For example, one embodiment of a fixed base robotic device has an agent delivery component disposed within the body of the device. In another implementation, the operational component can also include an arm or other positioning component. For example, the operational component can include an arm and a biopsy tool. Alternatively, the operational component can include a positioning component and any operational component as described above.

According to one embodiment, any of the components on any fixed base robotic device as described herein can be known, commercially available components.

In use, any of the fixed base robotic devices can be used in various surgical procedures. For example, a fixed base device can be used in combination with a laparoscopic surgical tool, wherein the device is adapted to fit through a port of the laparoscopic surgical tool and used for obtaining an internal image of an animal. In still other embodiments, the whole of the device is introduced into an open space to obtain internal images.

Alternatively, the fixed base robotic devices can be used in oral surgery and general dental procedures to provide an image of particularly difficult-to-access locations. Additionally, it will also be appreciated by those skilled in the art that the devices set forth herein can be applied to other functional disciplines wherein the device can be used to view difficult-to-access locations for industrial equipment and the like. For example, the device could be used to replace many industrial boroscopes.

Any of the robotic devices described herein can be used in various different surgical methods or procedures in which the device is used inside the patient's body. That is, the robotic devices can be used inside the patient's body to perform a surgical task or procedure and/or provide visual feedback to the user.

According to one embodiment, any of the mobile devices described above can be inserted entirely into the patient, wherein the patient can be any animal, including a human. In known laparoscopic procedures, the use of small incisions reduces patient trauma, but also limits the surgeon's ability to view and touch directly the surgical environment, resulting in poor sensory feedback, limited imaging, and limited mobility and dexterity. In contrast, the methods described herein using the various robotic devices inside the body can provide vision and surgical assistance and/or perform surgical procedures while the robotic device is not constrained by the entry incision.

In one embodiment, any of the above devices can be used inside an abdominal cavity in minimally invasive surgery, such as laparoscopy. Certain of the devices are sized and configured to fit through standard laparoscopic tools. According to one embodiment, the use of a robotic device inserted through one standard laparoscopy port eliminates the need for the second port required in standard laparoscopic procedures.

According to one embodiment, robotic devices as described herein having a camera can allow for planning of trocar insertion and tool placement, as well as for providing additional visual cues that will help the operator to explore and understand the surgical environment more easily and completely. Known laparoscopes use rigid, single view cameras with limited fields of view inserted through a small incision. To obtain a new perspective using this prior art device often requires the removal and reinsertion of the camera through another incision, thereby increasing patient risk. In contrast, the robotic devices with cameras as described herein provide one or more robots inside an abdominal cavity to deliver additional cavity images and easy adjustment of the field of view that improve the surgeon's geometric understanding of the surgical area. The ability to reposition a camera rapidly to arbitrary locations will help the surgeon maintain optimal orientation with respect to other tools.

In accordance with one implementation, any of the mobile robotic devices described herein can be used not only in traditional surgical environments such as hospitals, but also in forward environments such as battlefield situations.

Although the present invention has been described with reference to preferred embodiments, persons skilled in the art will recognize that changes may be made in form and detail without departing from the spirit and scope of the invention.

EXAMPLE 1

This example is an examination biopsy tool design for a mobile robotic device. The device should produce sufficient clamping and drawbar forces to biopsy porcine tissue.

To examine clamping and drawbar forces used during a biopsy, experimental biopsies were conducted. A biopsy forceps device that is commonly used for tissue sampling during esophago-gastroduodenoscopy (EGD) and colonoscopies was modified to measure cutting forces during tissue biopsy. These forceps 280, shown schematically in FIG. 17A, were composed of a grasper 282 on the distal end with a handle/lever system 284 on the proximal end. A flexible tube 286 was affixed to one side of the handle 284 and the other end was attached to the fulcrum point 288 of the biopsy grasper 282. A wire 290 enclosed in plastic (Teflon®) inside tube 286 was used to actuate the grasper 282. This wire 290 was affixed to the free end of the handle lever 284 and at the other end to the end of the grasper lever arm 292. Actuation of the handle lever 284 caused wire 290 to translate relative to the tube 286 and actuate the biopsy graspers 282. The tip of the forceps was equipped with a small spike 294 that penetrated the tissue during sampling.

Figure 17A:
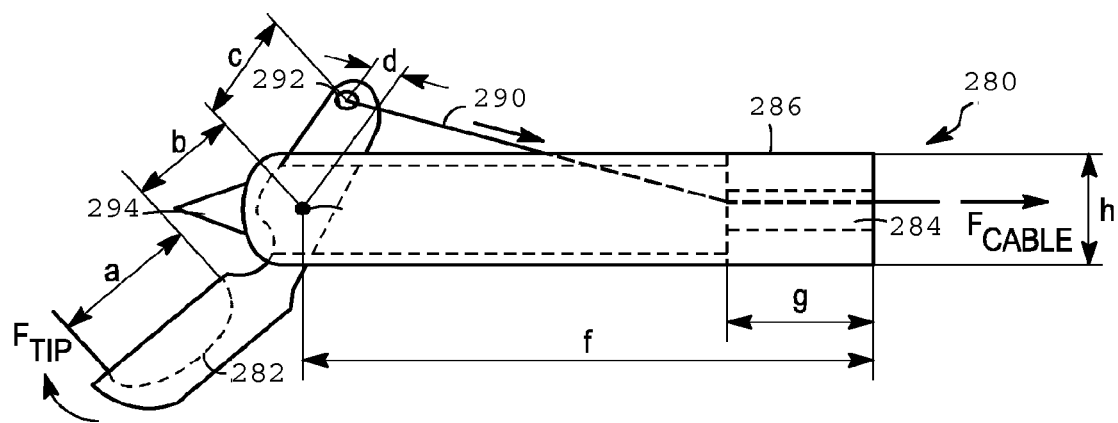
FIG. 17A is a schematic depiction of a forceps tool, according to one embodiment.

The diameter of the forceps (h) depicted in FIG. 17A was 2.4 mm. The dimensions of c, g and f were 2.1 mm, 2.0 mm, and 6.7 mm, respectively. The force at the tip of the grasper when the forceps were nearly closed was a function of the geometric design of the forceps.

$$F_{tip} = F_{cable}\left(\frac{d}{a+b}\right)$$

For a cable force of 10 N, the force at the tip was approximately 1.4 N for this design where a was 2.9 mm, b was 1.7 mm, and d was 0.65 mm. The maximum area of the forceps in contact with tissue during a biopsy was 0.3756 mm$^2$.

$$P_{contact} = \frac{F_{tip}}{A_{contact}}$$

Assuming an even distribution of force, the applied pressure was approximately 3.75 MPa. However, by taking a smaller "bite", the contact area was reduced and the pressure can be drastically increased and the required force was decreased.

Figure 17B:
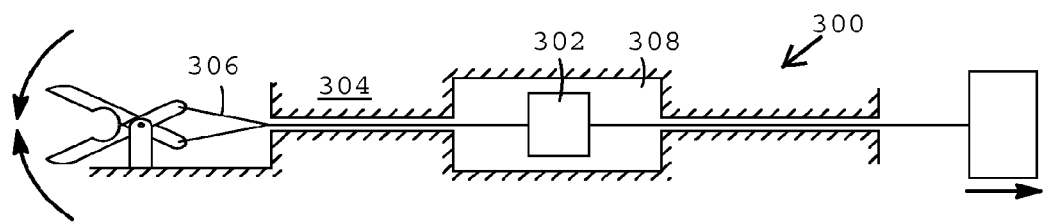
FIG. 17B is a schematic depiction of a biopsy tool modified to contain a load cell, according to one embodiment.

A normal biopsy device 300 was modified to contain a load cell 302 to measure clamping forces indirectly, as shown in FIG. 17B. The modifications made to this tool included cutting the tube 304 and wires 306 to place a load cell 302 in series with the wires 306 to measure tensile force when the wires 306 were actuated as shown in FIG. 17B. A plastic case 308 was built to connect the two free ends of the tube to retain the structure of the system, while the wires 306 were affixed to the free ends of the load cell 302. Using this design, the force in the cable was measured. Along with the above model, the force at the tip of the grasper was estimated while sampling sets of in vivo tissue using a porcine model.

Figure 18A:
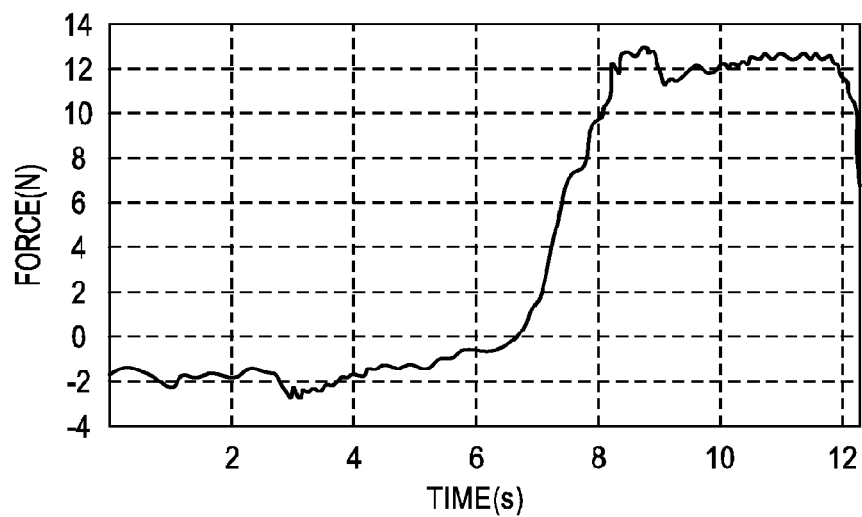
FIG. 18A shows measured cable force to biopsy in vivo porcine hepatic tissue, according to one embodiment.
Figure 18B:
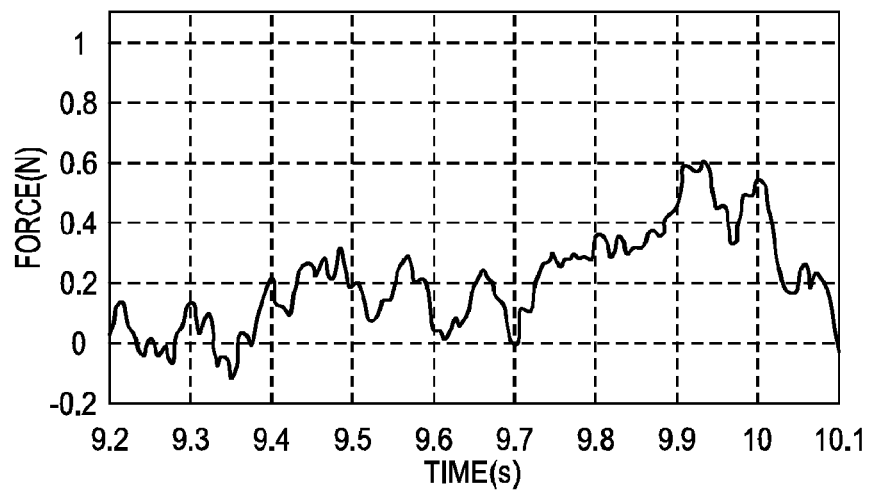
FIG. 18B shows measured extraction force to biopsy ex vivo bovine liver, according to one embodiment.

Measurements of cable force were made while sampling liver, omentum, small bowel and the abdominal wall of an anesthetized pig. Representative results for a liver biopsy are shown in FIGS. 18A and 18B. In one test, with results depicted in FIG. 18A, the initial negative offset was due to the slight compression in the cable to push the grasper jaws open before biopsy. The average maximum measured force to biopsy porcine liver for three samples was 12.0±0.4 N. These results are consistent in magnitude with other published results (Chanthasopeephan, et al. (2003) *Annals of Biomedical Engineering* 31:1372-1382) concerning forces sufficient to cut porcine liver.

Generally, biopsy forceps do not completely sever the tissue. When this is the case, the forceps are gently pulled to free the sample. This extraction force also needs to be produced by a biopsy robot. The magnitude of the extraction force needed to be determined so that a robot could be designed to provide sufficient drawbar force to free the sample.

A laboratory test jig was built to measure the force needed to free a biopsy sample of bovine liver. After clamping the sample with the biopsy forceps, a load cell attached to the handle of the device was gently pulled to free the sample while the tensile force was recorded. Representative results shown in FIG. 18B indicate that approximately 0.6 N of force is needed to extract bovine liver tissue with the use of the biopsy forceps.

Figure 19:
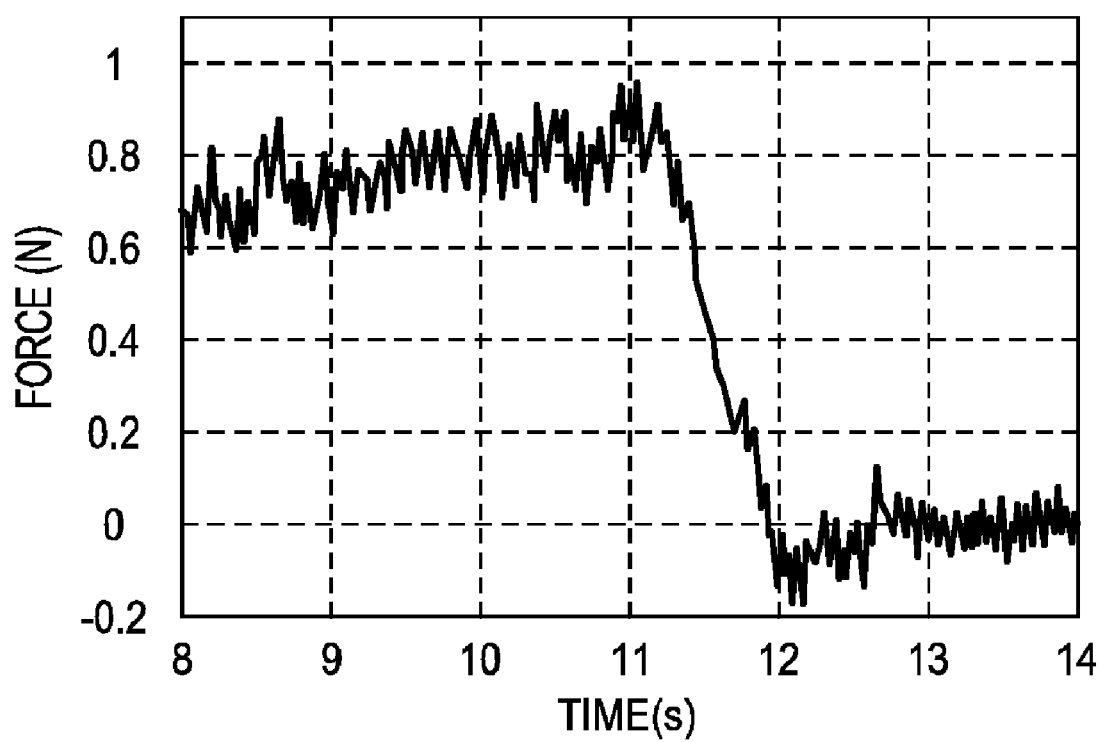
FIG. 19 shows drawbar force production from a robotic biopsy device where maximum drawbar force is produced at 11 seconds, as shown, before slowing down, according to one embodiment.

As indicated, a complete cut of the tissue is rarely achieved and some tearing of the sample is needed to extract the sample. To obtain a biopsy sample, the in vivo robot embodiment of the present example should produce enough drawbar force to pull the sample free. A biopsy robot similar to the devices shown in FIGS. 9A and 9B was tested in vivo and with excised bovine liver to measure drawbar forces. The biopsy grasper (tail of the robot) was attached to a stationary load cell. In the first test, for which results are depicted in FIG. 19, the robot speed was slowly increased as the drawbar force was recorded. After maximum drawbar force was achieved, around 11 seconds, the robot wheel motion was stopped. Results demonstrated that the robot was capable of producing approximately 0.9 N of drawbar force. This amount of force is 50% greater than the target of 0.6 N in the laboratory measurements, as shown in FIG. 18B. This drawbar force is therefore sufficient for sample extraction.

Figure 20:
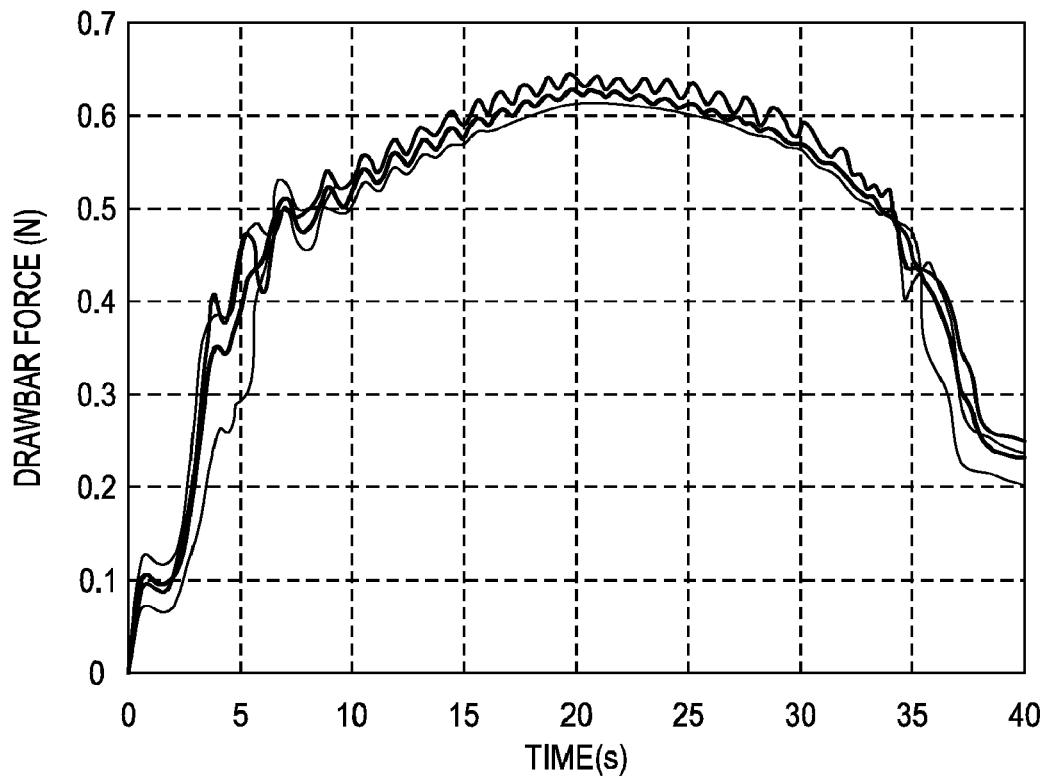
FIG. 20 shows drawbar force production from a robotic biopsy device in which the device speed was first slowly increased and then decreased, according to one embodiment.

In the second test, for which results are depicted in FIG. 20, the robot speed was first slowly increased and then decreased as the drawbar force was recorded. A pulse width modulated voltage signal to the wheel motors was linearly ramped from 0% to 100% during the first 20 seconds and then back to 0% during the second 20 seconds. This test was completed five times. The dark line is the average of all five tests. Results of this test demonstrate that the robot tested is capable of producing approximately 0.65 N of drawbar force. This amount of force is roughly 10% greater than the target of 0.6 N in the laboratory measurements.

Figure 21:
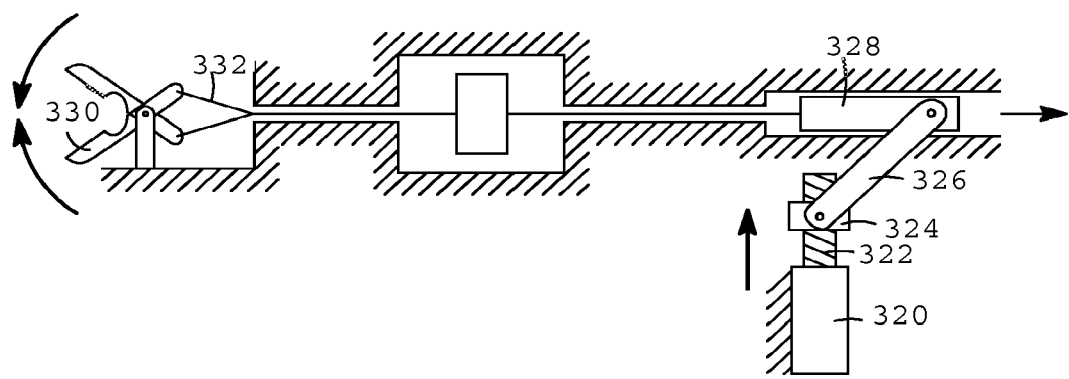
FIG. 21 depicts an actuation mechanism implemented on a biopsy robot for force production measurements, according to one embodiment.

As depicted in FIG. 21, an actuation mechanism was also developed to drive the biopsy grasper and the camera of the embodiment discussed in this example. The lead screw 322 was extended through the slider 328. The lead nut 324 was then allowed to translate far enough so that at the point of grasper 330 closure the linkage 326 approaches a mechanism singularity where output force is very large (i.e., at or approaching 0°). The slider 328 is a nearly hollow cylinder and the lead nut 324 and linkage 326 are inside the slider 328 when the linkage is near its singularity. The grasper wires 332 are attached to slider 328 as is either the camera lens or image sensor. This provides the camera an adjustable-focus feature necessary in the in vivo environment.

A direct current motor 320 drives the lead screw 322 vertically as the linkage 326 transforms the vertical motion of the lead nut 324 to the horizontal translation of the slider 328. This allows for a large mechanical advantage at the point when the graspers are nearly closed.

Figure 22:
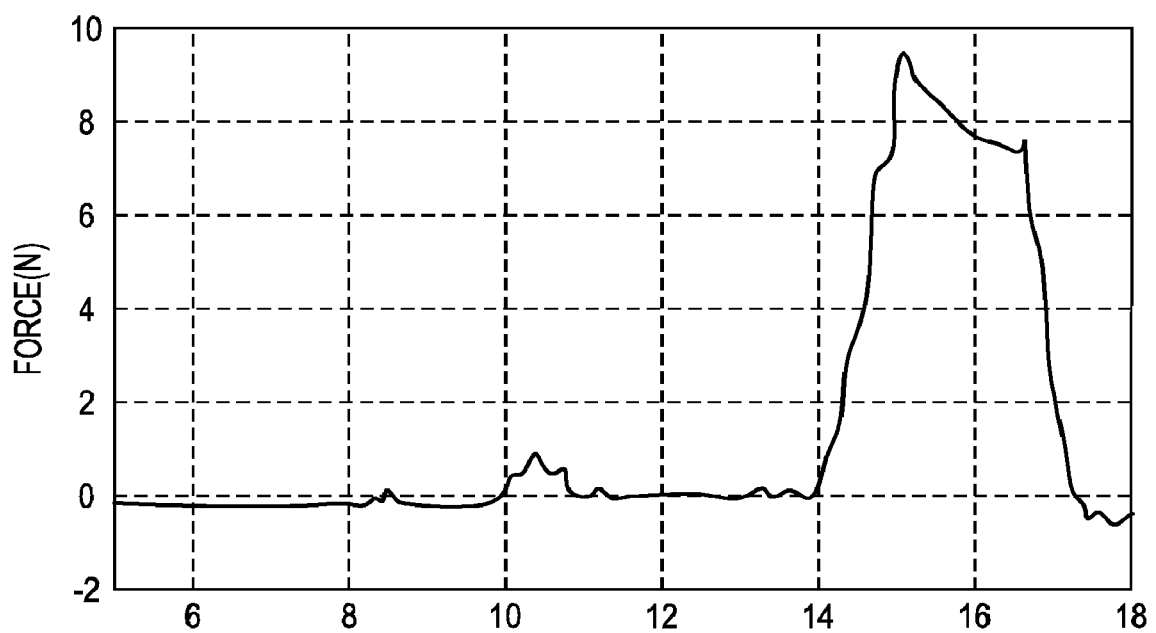
FIG. 22 shows force production measured from the robot biopsy mechanism depicted in FIG. 21, according to one embodiment.

Force measurements were made in the laboratory to determine the maximum amount of force that could be produced using the biopsy robot embodiment of this example. Representative results from these tests are shown in FIG. 22. The average maximum force produced for three samples was 9.6±0.1 N. This force was about 16% smaller than the 12 N measured during one in vivo test as described herein, and about 7% larger than the 9 N measured during the second in vivo test as described herein. However, the 12 N merely represents the force that was applied. It does not represent the minimum force required to biopsy the tissue. Without being limited by theory, it is probable that the surgeon performed the biopsy and continued to increase the force and merely "squeezed" the sample. The surgeon applied what was known to be a sufficient force rather than a minimum force. The required force could also be largely reduced by simply taking a smaller biopsy sample. Reducing the contact area by 16% would produce the same applied stress.

In vivo mobility testing with the embodiment discussed herein indicated that the wheel design of the instant embodiment produces sufficient drawbar forces to maneuver within the abdominal environment, allowing the robot to traverse all of the abdominal organs (liver, spleen, small and large bowel), as well as climb organs two to three times its height. These tests were performed without causing any visible tissue damage.

After exploring the abdominal environment, the biopsy mechanism described in this example was used to acquire three samples of hepatic tissue from the liver of the animal. The robot camera was used to find a suitable sample site. The biopsy graspers were opened and the sample site was penetrated with the biopsy forceps' spike. Then the graspers were actuated. This cut nearly all of tissue sample free. The robot was then driven slowly away from the sample site thereby pulling free the tissue sample. This tissue sample was then retrieved after robot extraction through the entry incision. This demonstrated the success of a one-port biopsy and successful tissue manipulation by an in vivo robot, according to one embodiment.

EXAMPLE 2

Figure 23:
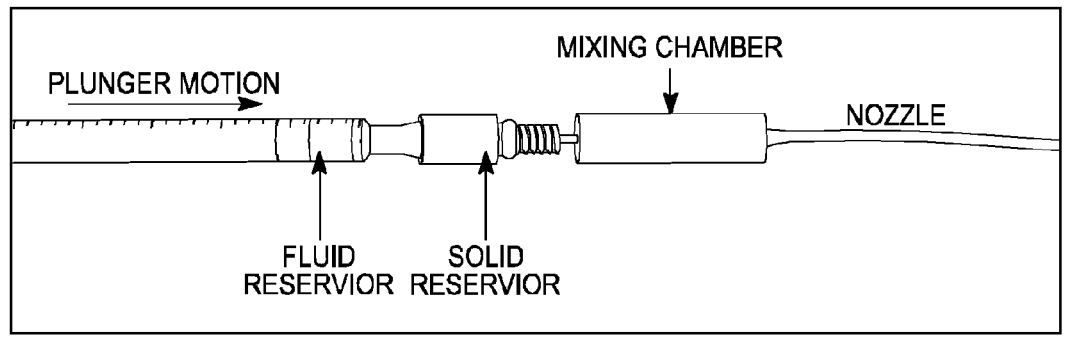
FIG. 23 depicts a laboratory two-component drug delivery system, according to one embodiment.

A laboratory two-component drug delivery system is shown in FIG. 23 that incorporates two drug storage reservoirs. The fluid reservoir, adapted from a standard syringe, is used to hold a drug component in liquid form. The solid reservoir stores a second drug component in powdered form. As force is applied to the plunger, the liquid component flows through the reservoir holding the solid component. A partially mixed solution then flows into a chamber where the mixing process is completed. The activated compound then flows through the delivery nozzle to the targeted site.

Figure 24:
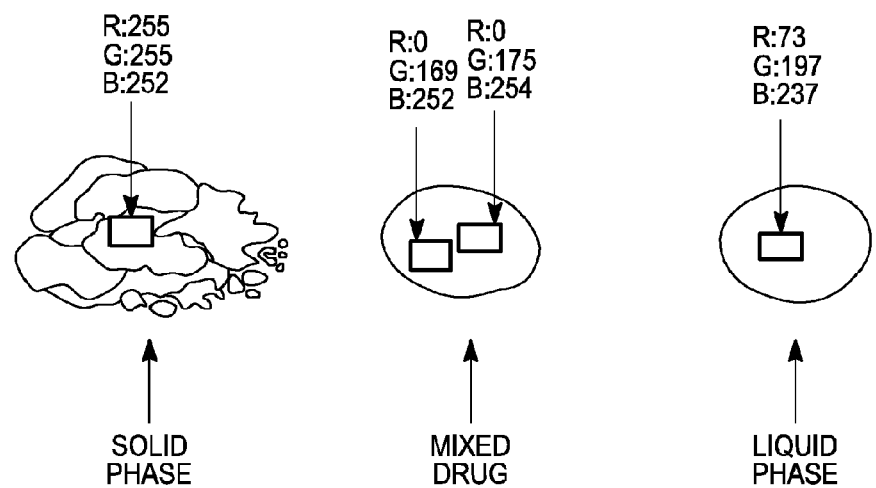
FIG. 24 depict representative results of mixing two drug components, one solid and one liquid, according to one embodiment.

The ability of this system to adequately mix liquid and solid components of a drug was evaluated in a series of bench top experiments. The liquid and solid drug components were simulated using commonly available materials (e.g., corn starch, dyed saline solution, etc). One visual metric of mixing efficiency is the color uniformity of the mixture as determined by measuring the RGB color components of the mixture using image processing software. Representative results are shown in FIG. 24. The images on the left and right show the RGB values for the solid and liquid components prior to mixing, respectively. The image in the center shows the resulting mixture. The similarity of the RGB color values for two representative areas of the mixture is indicative of uniform mixing of the two components.

Bench top tests were also conducted to determine the force that could be applied by an actuation mechanism that could be incorporated into this type of drug delivery tool. One type of mechanism might use a permanent magnet direct current motor (MicroMo, 2005) with a lead screw mounted on the motor shaft. Rotation of the lead screw would move a lead nut attached to the fluid reservoir plunger in and out to dispense the two drug components. This concept was implemented in a test jig 180, illustrated in FIG. 12, that includes a load cell 182 for measuring the applied force created by the motor 184 to move the plunger 186. Force measurements were made in the lab to determine the maximum force that could be produced using this type of actuator design. Representative results from these tests indicate that the average maximum force produced is approximately 10.0 N.

Nagelschmidt (1999) found that the maximum force required to mix and dispense fibrin-based hemostatic agents through 1 mm diameter catheters 27 cm long was less than 5 N. These results strongly suggest that the actuation mechanism described above will generate sufficient forces to deliver dual component fibrin-based hemostatic agents.

What is claimed is:

1. A mobile robotic device, comprising:
   (a) a body configured to be disposed within a patient cavity;
   (b) a translational mobility component coupled with the body;
   (c) an actuator coupled with the translational mobility component;
   (d) a power source coupled with the actuator;
   (e) a controller component coupled with the actuator;
   (f) an agent delivery component associated with the body, wherein the mobility component is configured to apply translational pressure on a surface for purposes of mobility or immobility.

2. The device of claim 1, wherein the agent delivery component is disposed within the body.

3. The device of claim 1, wherein the agent delivery component is configured to deliver an agent, wherein the agent is a hemostatic agent.

4. The device of claim 1, wherein the agent delivery component comprises:
   (a) at least one agent reservoir; and
   (b) a discharge component in fluidic communication with the at least one reservoir.

5. The device of claim 4, wherein the discharge component is a mixing and discharge component comprising:
   (a) at least one delivery tube in fluidic communication with the at least one reservoir;
   (b) a manifold in fluidic communication with the at least one delivery tube; and
   (c) a cannula in fluidic communication with the manifold.

6. The device of claim 1, further comprising at least one imaging component associated with the body.

7. The device of claim 1, wherein the controller component is wirelessly coupled with the actuator.

8. The device of claim 1, wherein the controller component is coupled with the actuator via a flexible connection component.

9. The device of claim 1, further comprising an operational component operably associated with the body.

10. The device of claim 9, wherein the operational component is a biopsy tool.

11. The device of claim 9, wherein the operational component is a sensor.

12. A method of performing a procedure inside a patient, the method comprising:
    positioning a robotic device in a cavity inside the patient, wherein the robotic device comprises:
    (a) a body configured to be disposed within a patient cavity;
    (b) a mobility component coupled with the body;
    (c) an actuator coupled with the mobility component;
    (d) a power source coupled with the actuator;
    (e) a controller component coupled with the actuator; and
    (f) an agent delivery component associated with the body, the agent delivery component comprising:
       (i) at least one agent reservoir; and
       (ii) a mixing and discharge component in fluidic communication with the at least one reservoir;
    operating the controller component to cause the mobility component to move the robotic device to a desired location within the cavity; and
    delivering an agent to the desired location with the agent delivery component.

13. The method of claim 12, wherein delivering the agent to the desired location further comprises operating the controller component to cause the agent delivery component to deliver the agent.

14. The method of claim 12, wherein the robotic device further comprises an operational component operably coupled with the body.

15. The method of claim 14, wherein the operational component is a biopsy tool.

16. The method of claim 15, further comprising using the biopsy tool to obtain a biopsy sample from the desired location prior to delivering the agent.

* * * * *